United States Patent
Frock et al.

(10) Patent No.: US 11,534,310 B2
(45) Date of Patent: Dec. 27, 2022

(54) INTERSPINOUS PROCESS IMPLANT

(71) Applicant: Spinal Simplicity, LLC, Overland Park, KS (US)

(72) Inventors: Melissa Frock, Lenexa, KS (US); Adam Frock, Lenexa, KS (US); Todd Moseley, Olathe, KS (US); Adam Rogers, Overland Park, KS (US); Jeff Slover, Lee's Summit, MO (US)

(73) Assignee: Spinal Simplicity, LLC, Overland Park, KS (US)

( * ) Notice: Subject to any disclaimer, the term of this patent is extended or adjusted under 35 U.S.C. 154(b) by 0 days.

(21) Appl. No.: 17/677,677

(22) Filed: Feb. 22, 2022

(65) Prior Publication Data

US 2022/0175548 A1 Jun. 9, 2022

Related U.S. Application Data

(63) Continuation-in-part of application No. 17/389,418, filed on Jul. 30, 2021, now Pat. No. 11,311,389, which is a continuation of application No. 16/998,171, filed on Aug. 20, 2020, now Pat. No. 11,311,388.

(51) Int. Cl.
*A61F 2/44* (2006.01)
*A61B 17/70* (2006.01)
*A61F 2/30* (2006.01)

(52) U.S. Cl.
CPC ........ *A61F 2/4455* (2013.01); *A61B 17/7062* (2013.01); *A61F 2002/30062* (2013.01); *A61F 2002/30957* (2013.01); *A61F 2002/30985* (2013.01); *A61F 2310/00023* (2013.01); *A61F 2310/00796* (2013.01)

(58) Field of Classification Search
CPC .................. A61F 2/4405; A61B 17/7062–707
See application file for complete search history.

(56) References Cited

U.S. PATENT DOCUMENTS

| | | |
|---|---|---|
| 4,573,844 A | 3/1986 | Smith |
| 5,098,433 A | 3/1992 | Freedland |
| 6,419,676 B1 | 7/2002 | Zucherman et al. |
| 7,226,261 B1 | 6/2007 | Bristol |
| 8,343,190 B1 | 1/2013 | Mueller et al. |
| 8,945,184 B2 | 2/2015 | Hess et al. |
| 9,314,276 B2 | 4/2016 | Hess et al. |
| 9,545,267 B2 | 1/2017 | Seifert et al. |
| 9,757,164 B2 | 9/2017 | Hess et al. |

(Continued)

OTHER PUBLICATIONS

PCT Application No. PCT/US2021/044609 International Search Report and Written Opinion, dated Dec. 21, 2021.

*Primary Examiner* — Nicholas J Plionis
(74) *Attorney, Agent, or Firm* — Erise IP, P.A.

(57) ABSTRACT

A system and method for providing a spinal implant having a main body, a proximal anchor, a distal anchor, and an internal plunger. The proximal anchor comprises a nut having an internal bore. The distal anchor comprises a plurality of wings having a first closed configuration and a second open configuration. The internal plunger is housed within a central bore of the main body. The distal end of the internal plunger is operatively connected to the first wing and the second wing to selectively move the wings between the first closed configuration and the second open configuration, and vice versa.

20 Claims, 22 Drawing Sheets

(56) References Cited

U.S. PATENT DOCUMENTS

| | | |
|---|---|---|
| 9,861,399 B2 | 1/2018 | Rogers et al. |
| 9,907,581 B2 | 3/2018 | Hess et al. |
| 10,420,591 B2 | 9/2019 | Snell et al. |
| 2004/0208722 A1 | 10/2004 | Kuenzel |
| 2005/0129482 A1 | 6/2005 | Wang |
| 2005/0182416 A1* | 8/2005 | Lim .................... A61B 17/025 606/90 |
| 2006/0085070 A1 | 4/2006 | Kim |
| 2008/0108990 A1 | 5/2008 | Mitchell et al. |
| 2008/0147190 A1 | 6/2008 | Dewey et al. |
| 2008/0183211 A1 | 7/2008 | Lamborne et al. |
| 2008/0243250 A1 | 10/2008 | Seifert et al. |
| 2010/0057130 A1 | 3/2010 | Yue |
| 2010/0152775 A1 | 6/2010 | Seifert et al. |
| 2010/0234889 A1* | 9/2010 | Hess .................. A61B 17/7062 606/279 |
| 2014/0194930 A1 | 7/2014 | Hess et al. |
| 2015/0112387 A1 | 4/2015 | Hess et al. |
| 2016/0166396 A1* | 6/2016 | McClintock ............ A61F 2/446 623/17.16 |
| 2020/0015864 A1 | 1/2020 | Snell et al. |
| 2022/0054279 A1 | 2/2022 | Frock et al. |
| 2022/0054280 A1 | 2/2022 | Frock et al. |

\* cited by examiner

INTERSPINOUS PROCESS IMPLANT

RELATED APPLICATION

This application is a continuation-in-part of U.S. patent application Ser. No. 17/389,418 filed Jul. 30, 2021, which is a continuation of U.S. patent application Ser. No. 16/998,171, filed Aug. 20, 2020, the disclosures of which are incorporated herein by reference.

BACKGROUND

1. Field

Embodiments of the invention relate to spinal implants. More specifically, embodiments of the invention relate to a percutaneously or posteriorly introduced spinous process implant and fusion device.

2. Related Art

The spine consists of a column of twenty-four vertebrae that extend from the skull to the hips. Discs of soft tissue are disposed between adjacent vertebrae. In addition, the spine encloses and protects the spinal cord, defining a bony channel around the spinal cord, called the spinal canal. There is normally a space between the spinal cord and the borders of the spinal canal so that the spinal cord and the nerves associated therewith are not pinched.

Over time, the ligaments and bone that surround the spinal canal can thicken and harden, resulting in a narrowing of the spinal canal and compression of the spinal cord or nerve roots. This condition is called spinal stenosis, which results in pain and numbness in the back and legs, weakness and/or a loss of balance. These symptoms often increase after walking or standing for a period of time.

There are a number of non-surgical treatments for spinal stenosis. These include non-steroidal anti-inflammatory drugs to reduce the swelling and pain, and corticosteroid injections to reduce swelling and treat acute pain. While some patients may experience relief from symptoms of spinal stenosis with such treatments, many do not, and thus turn to surgical treatment. The most common surgical procedure for treating spinal stenosis is decompressive laminectomy, which involves removal of parts of the vertebrae. The goal of the procedure is to relieve pressure on the spinal cord and nerves by increasing the area of the spinal canal.

Interspinous process decompression (IPD) is a less invasive surgical procedure for treating spinal stenosis. With IPD surgery, there is no removal of bone or soft tissue. Instead, an implant or spacer device is positioned behind the spinal cord or nerves and between the interspinous processes that protrude from the vertebrae in the lower back.

Examples of a particularly useful interspinous process implant and fusion devices are disclosed in commonly assigned U.S. Pat. Nos. 9,861,399, 8,945,184; 9,314,276, 9,907,581, and 9,757,164, the disclosures of which are all incorporated herein by reference in their entirety.

The invention provides an improvement over prior interspinous implant devices by constructing an implant that is substantially shorter in length than prior devices. This will advantageously reduce the overall size and profile of the device, thereby making implantation safer and easier.

The construction of the implant according to an embodiment of the invention also allows for easier removal of the device after implantation, if desired. The ability of the surgeon to both selectively open and close the wings of the device is another advantage over prior devices. Because the wings can be closed after implantation, the implant of the invention can be removed by the same small lateral incision through which it was originally inserted. Removal of prior devices generally requires an additional posterior incision to manually close the wings before the device can be extracted.

Additionally, the device of the invention does not require a removable end piece. This improves the safety and ease of the procedure by reducing the number of steps in the implantation process. Fewer separable parts of the implant also reduces cost and simplifies manufacturing.

SUMMARY

Embodiments of the invention solve the above-mentioned problems by providing a system and method for minimally invasive spinal fusion.

A first embodiment of the invention is directed to a spinal implant comprising: a main body, a proximal anchor, a distal anchor, and an internal plunger. The main body has an outer surface, a central bore therein, a proximal end, a distal end, and a longitudinal axis extending therebetween. The proximal anchor comprises a nut having a proximal side, a distal side, and an internal bore. The distal anchor comprises a plurality of wings having a first closed configuration and a second open configuration, wherein the plurality of wings comprises a first wing and a second wing. The internal plunger has a proximal end, a distal end, and is housed within the central bore of the main body. The distal end of the internal plunger is operatively connected to the first wing and the second wing to selectively move the plurality of wings between the first closed configuration and the second open configuration.

A further embodiment of the invention is directed to a spinal implant comprising a main body, a proximal anchor, a distal anchor, and a linkage assembly. The main body has an outer surface, a central bore therein, a proximal end, a distal end, and a longitudinal axis extending therebetween. The main body includes external threads on at a least a portion of the outer surface. The proximal anchor comprises a nut having a proximal side, a distal side, and an internal bore having internal threads. The distal anchor comprises a first wing and a second wing configured to be selectively opened and closed. The linkage assembly connects the first wing and the second wing to the main body.

Another embodiment of the invention is directed to a method of placing a spinal implant at a treatment site comprising: providing a spinal implant in a first closed configuration; placing the spinal implant in a patient at a desired treatment site; and sliding the internal plunger distally along the longitudinal axis to move the plurality of wings to the second open configuration. The method may further comprise sliding the internal plunger proximally along the longitudinal axis to move the plurality of wings to the first closed configuration to withdraw the spinal implant from the patient.

This summary is provided to introduce a selection of concepts in a simplified form that are further described below in the detailed description. This summary is not intended to identify key features or essential features of the claimed subject matter, nor is it intended to be used to limit the scope of the claimed subject matter. Other aspects and advantages of the invention will be apparent from the following detailed description of the embodiments and the accompanying drawing figures.

BRIEF DESCRIPTION OF THE DRAWING FIGURES

Embodiments of the invention are described in detail below with reference to the attached drawing figures, wherein.

Figure 1:
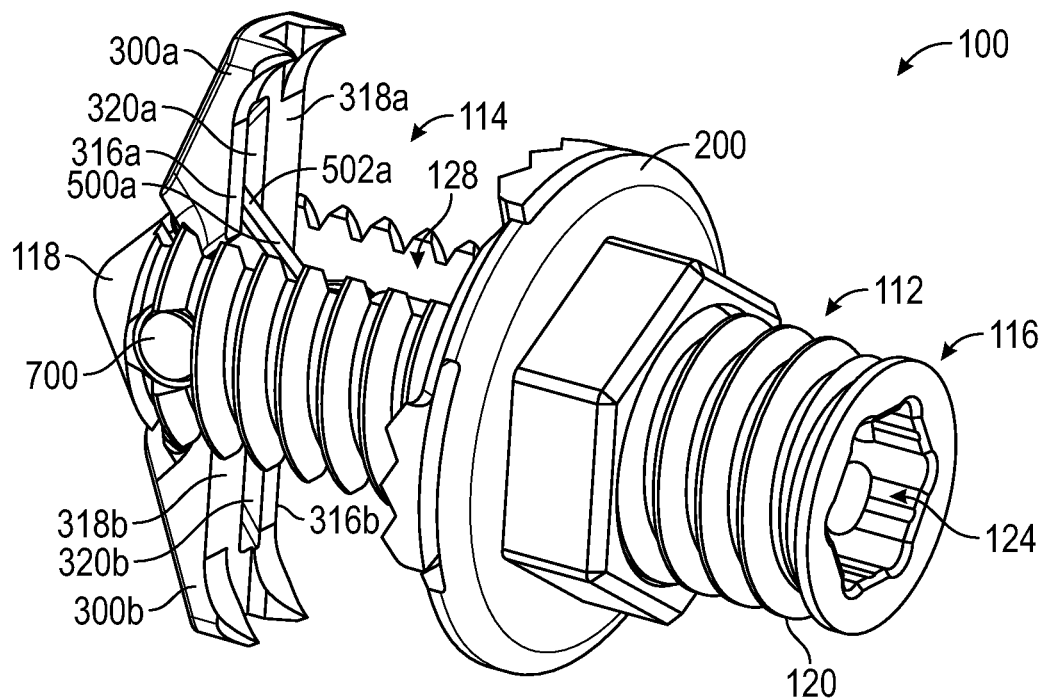
FIG. 1 is a perspective view of a first embodiment of the implant of the invention in an open configuration.

The drawing figures do not limit the invention to the specific embodiments disclosed and described herein. The drawings are not necessarily to scale, emphasis instead being placed upon clearly illustrating the principles of the invention.

DETAILED DESCRIPTION

The following detailed description references the accompanying drawings that illustrate specific embodiments in which the invention can be practiced. The embodiments are intended to describe aspects of the invention in sufficient detail to enable those skilled in the art to practice the invention. Other embodiments can be utilized and changes can be made without departing from the scope of the invention. The following detailed description is, therefore, not to be taken in a limiting sense. The scope of the invention is defined only by the appended claims, along with the full scope of equivalents to which such claims are entitled.

In this description, references to "one embodiment," "an embodiment," or "embodiments" mean that the feature or features being referred to are included in at least one embodiment of the technology. Separate references to "one embodiment," "an embodiment," or "embodiments" in this description do not necessarily refer to the same embodiment and are also not mutually exclusive unless so stated and/or except as will be readily apparent to those skilled in the art from the description. For example, a feature, structure, act, etc. described in one embodiment may also be included in other embodiments, but is not necessarily included. Thus, the technology can include a variety of combinations and/or integrations of the embodiments described herein.

Embodiments of the invention are directed to a minimally invasive interspinous-interlaminar fusion device for the temporary fixation of the thoracic, lumbar, and sacral spine while waiting for bony fusion to occur. The implant can be attached to the posterior non-cervical spine at the spinous processes to provide immobilization and stabilization of the spinal segments. A threaded main body of the implant provides controlled distraction.

One embodiment of the invention is shown in FIG. 1, which illustrates an interspinous process implant 100 in an open configuration. Implant 100 may include a main body 112 having a distal end 114 and a proximal end 116. Implant 100 further includes a nut 200 on the proximal end 116 of main body 112 and extendable first and second wings 300a, 300b on the distal end 114 of main body 112. As can be seen in the cross-sectional view of FIG. 2, implant 100 further includes a plunger 400 and first and second linkages 500a, 500b for operatively connecting first and second wings 300a, 300b to main body 112, as will be described herein.

Figure 3:
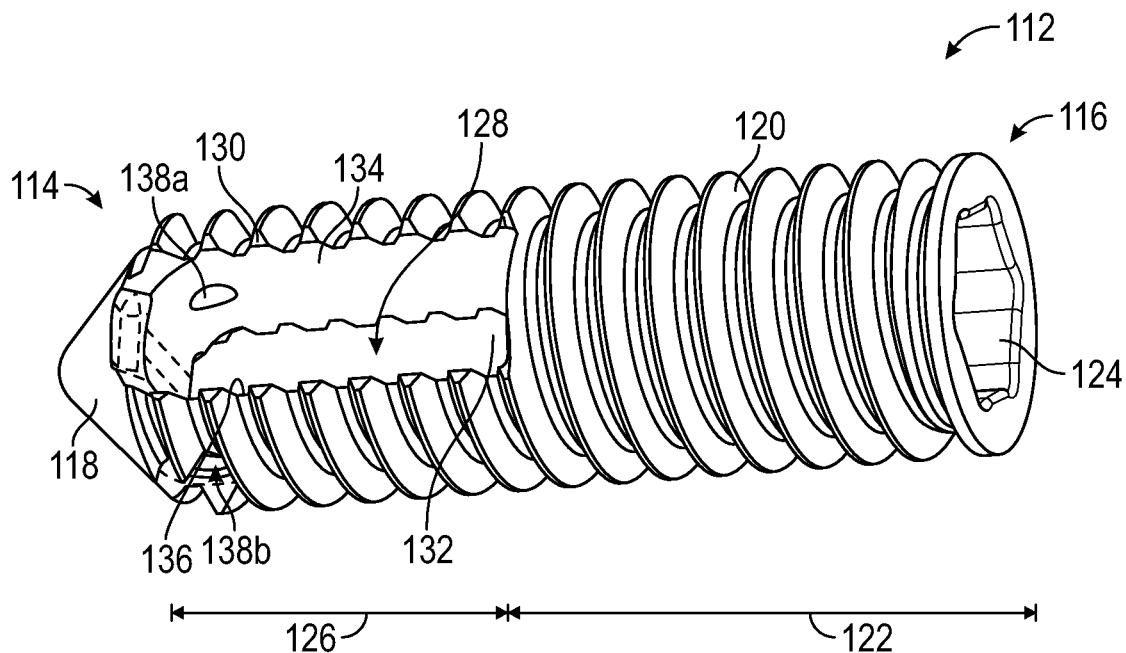
FIG. 3 is a perspective view of an embodiment of the main body of the invention.

FIG. 3 illustrates an embodiment of main body 112. Distal end 114 includes a conical distal tip 118 having a rounded distalmost end. In some embodiments, the conical distal tip has a sharp pointed distalmost end. In some embodiments, main body 112 includes helical threads 120 on an exterior surface thereof. In some embodiments, main body 112 may alternatively or additionally include cutting threads or box threads. Helical threads 120 may be provided along the entire exterior surface of main body 112 or along only a portion of the exterior surface of main body 112. In some embodiments, the threads may have a depth of about 0.5 to about 3.0 mm, an angle of about 45° to about 100°, and a spacing of about 1.0 mm to about 4.0 mm. In some embodiment, the threads may have a depth of about 1.0 mm, an angle of about 60°, and a spacing of about 1.75 mm. In some embodiments, distal tip 118 has a smooth exterior surface without any threads thereon. In some embodiments, the distal tip 118 is a solid tip for providing strength during insertion of the implant 100.

Main body 112 further includes a proximal portion 122 extending from the proximal end 116, having hollow bore 124. The majority of hollow bore 124 may be substantially cylindrical. Proximal end of hollow bore 124 may have a particular shape such as a hexagonal perimeter configured to receive an insertion tool therein (not shown). Proximal end of hollow bore 124 may also include detents 125 adapted for receiving and locking a distal end of an insertion tool therein (not shown).

Main body 112 also includes a distal portion 126 extending from the distal end 114, having a substantially rectangular window 128. The window 128 extends from a first lateral side 130 to a second lateral side 132, a top flat interior wall 134, and a bottom flat interior wall 136. At the distal end of the window 128, top wall 134 includes an opening 138a therethrough and bottom wall 136 includes an opening 138b therethrough. Openings 138a, 138b are configured to receive a bolt 700 for mounting wings 300a, 300b, as seen in FIG. 4.

Figure 4:
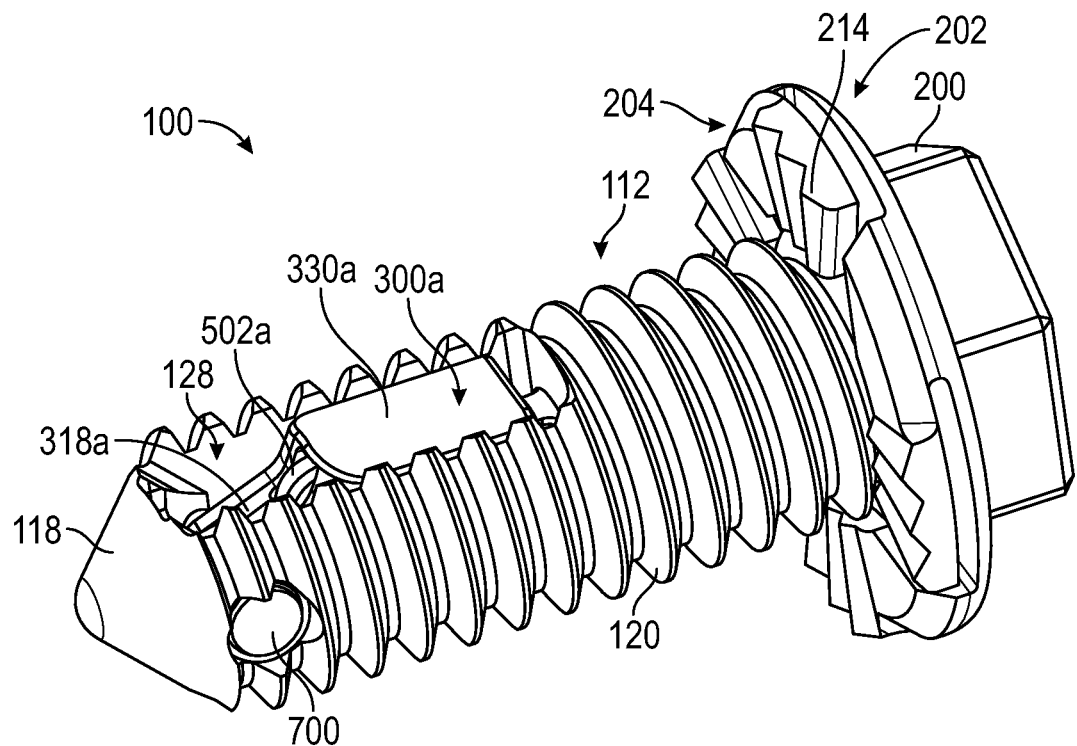
FIG. 4 is a perspective view of the first embodiment of the implant of the invention in the closed configuration.
Figure 15:
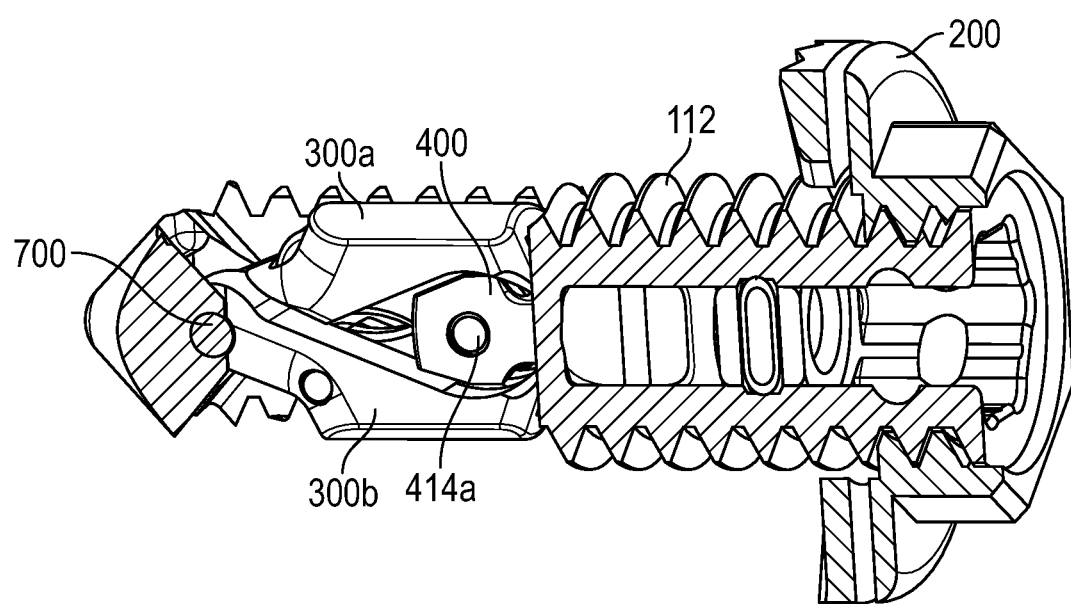
FIG. 15 is another cross-sectional view of the first embodiment of the implant of the invention in the closed configuration.

FIGS. 4 and 15 illustrate implant 100 with wings 300a, 300b in a closed configuration. Window 128 of main body 112 is configured to house a distal portion of the plunger 400, first and second linkages 500a, 500b, and first and second wings 300a, 300b when in the closed configuration.

Figure 2:
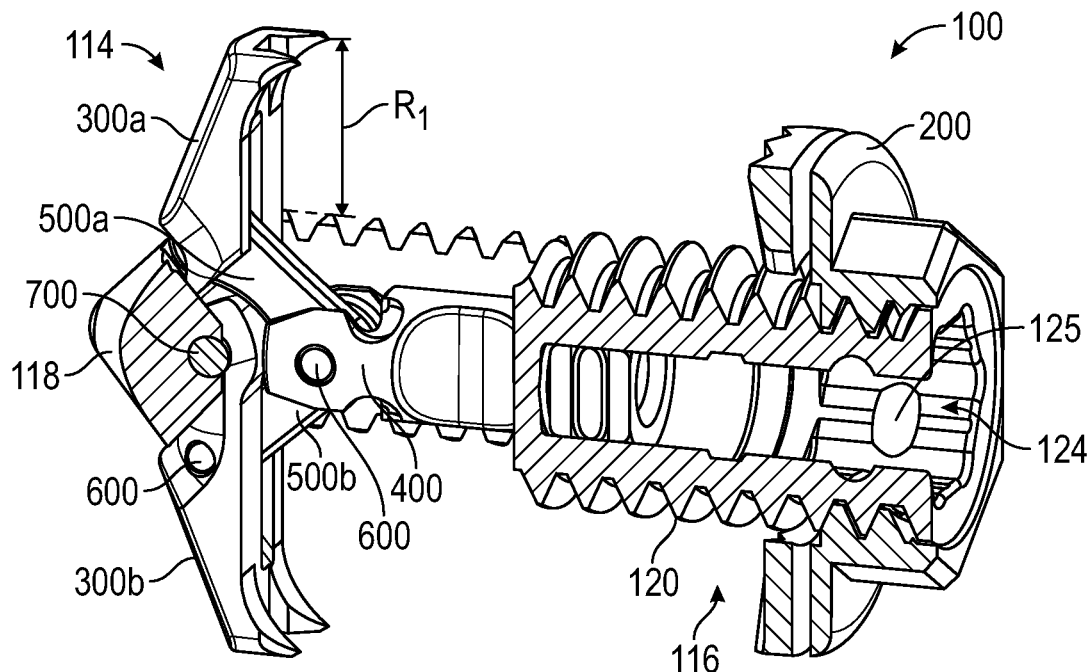
FIG. 2 is a cross-sectional view of the first embodiment of the implant of the invention in an open configuration.
Figure 5:
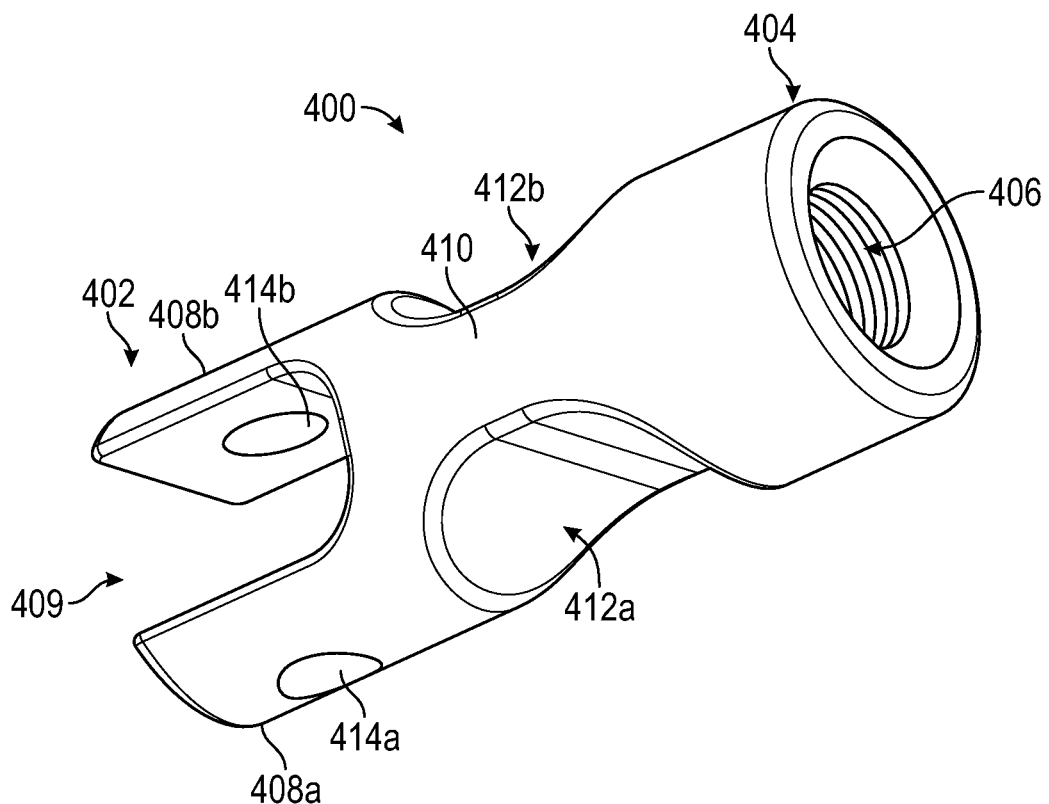
FIG. 5 is a perspective view of an embodiment of a plunger of the invention.

FIG. 5 illustrates an embodiment of plunger 400. Plunger 400 has a distal end 402 and proximal end 404. Proximal end 404 is configured to be located within the bore 124 of main body 112 and distal end 402 is configured to be located within the window 128 of the main body 112, as seen in FIG. 2. Plunger 400 can be moved longitudinally within the bore 124 and window 128 to open and close the wings 300a, 300b, as will be described further below.

With respect to FIG. 5, proximal end of plunger 400 has a central bore 406 for receiving an inserter device (not shown) therein. In some embodiments, central bore 406 of plunger 400 may be threaded to cooperate with threading on an inserter device. Plunger 400 has a substantially Y-shaped construction, having a first arm 408a and a second arm 408b extending from a solid central portion 410. First arm 408a and second arm 408b have a space 409 therebetween. Central portion 410 has two opposed curved indentations 412a, 412b on an outer side, as can be seen in FIG. 5. First arm 408a and second arm 408b each have a hole 414a, 414b extending therethrough for receiving a mounting pin 600 therein. In order to connect wings 300a, 300b to the plunger 400, linkages 500a, 500b are mounted within the space 409 between the arms 408a, 408b. In some embodiments, plunger 400 may have a total length of about 13 mm to about 15 mm. In some embodiments, plunger 400 may have a total length of about 13.9 mm. First and second arms 408a, 408b may have a length of about 4-5 mm. First and second arms 408a, 408b may have a length of about 4.5 mm.

In an alternative embodiment, a plunger may have two heads having a T-shape or dove-tail feature that rides in a mating grove on the underside of wings 300a, 300b. In a further alternative embodiment, a plunger may be connected by an umbrella-like feature having linkages that ride within a groove on an underside of the wings 300a, 300b.

Figure 6A:
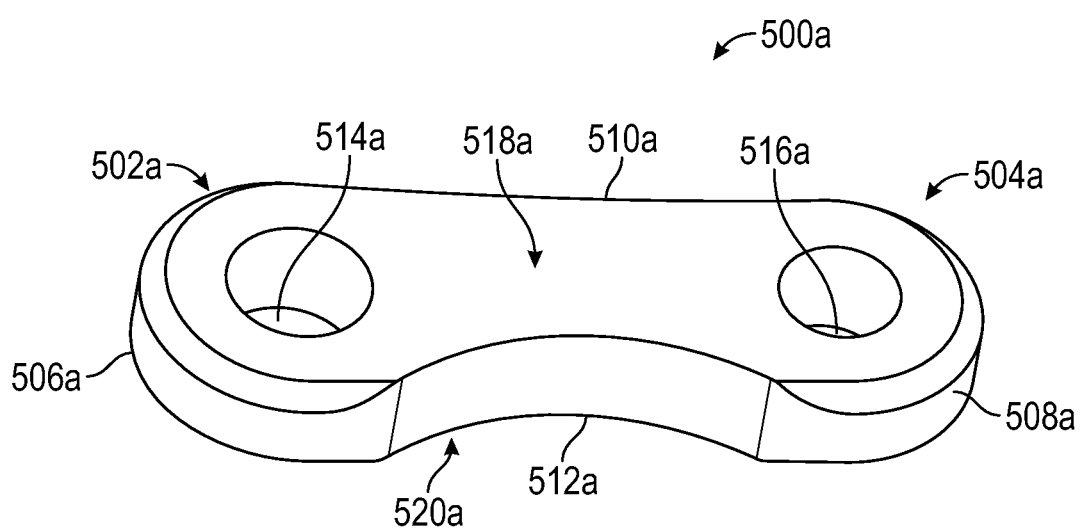
FIG. 6A is a perspective view of an embodiment of a first linkage of the invention.
Figure 6B:
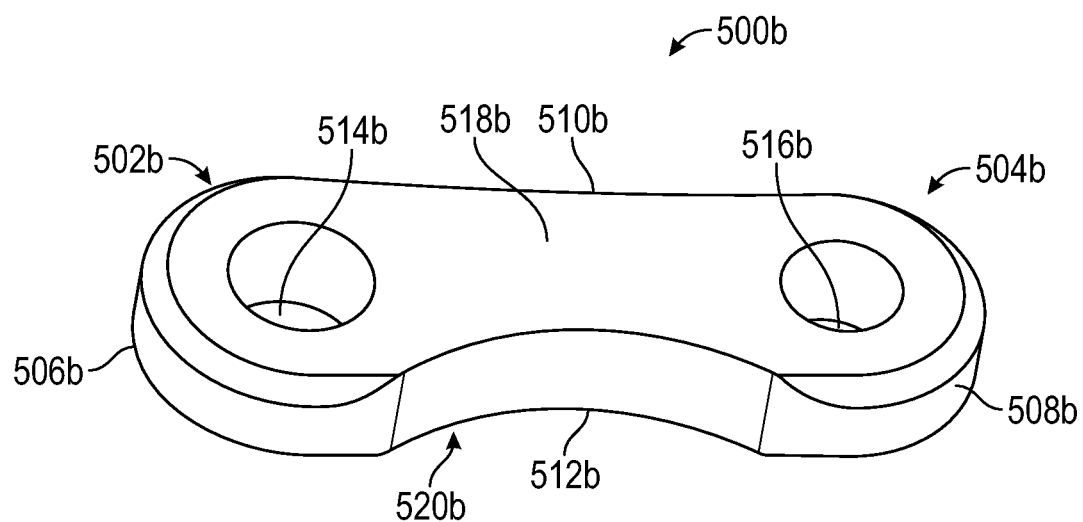
FIG. 6B is a perspective view of an embodiment of a second linkage of the invention.

FIGS. 6A and 6B illustrate an embodiment of first and second linkages 500a, 500b, respectively. First linkage 500a has a first end 502a and a second end 504a. In some embodiments, first linkage 500a is substantially oval shaped with first end 502a having a rounded edge 506a, and second end 504a having a rounded edge 508a. First linkage 500a further includes a straight top edge 510a and an indented curved bottom edge 512a. First end 502a includes a hole 514a extending therethrough and second end 504a includes a hole 516a extending therethrough. Holes 514a and 516a are each configured to receive a mounting pin 600 therein. First linkage 500a includes a substantially planar top surface 518a and a substantially planar bottom surface 520a.

As can be seen in FIG. 6B, second linkage 500b is substantially identical to first linkage 500a. Second linkage 500b has a first end 502b and a second end 504b. In some embodiments, second linkage 500b is substantially oval shaped with first end 502b having a rounded edge 506b, and second end 504b having a rounded edge 508b. Second linkage 500b further includes a straight top edge 510b and an indented curved bottom edge 512b. First end 502b includes a hole 514b extending therethrough and second end 504b includes a hole 516b extending therethrough. Holes 514b and 516b are each configured to receive a mounting pin 600 therein. Second linkage 500b includes a substantially planar top surface 518b and a substantially planar bottom surface 520b. In some embodiments, first and second linkages 500a, 500b may have a length of about 8 mm to 10 mm. In some embodiments, first and second linkages 500a, 500b may have a length of about 9.2 mm. The distance between the holes 514a and 516a (and 514b and 516b) may be about 5 mm to about 7 mm. The distance between the holes 514a and 516a (and 514b and 516b) may be about 5.9 mm. Curved bottom edges 512a, 512b may have a curvature with a radius of about 3.5 mm.

Figure 7:
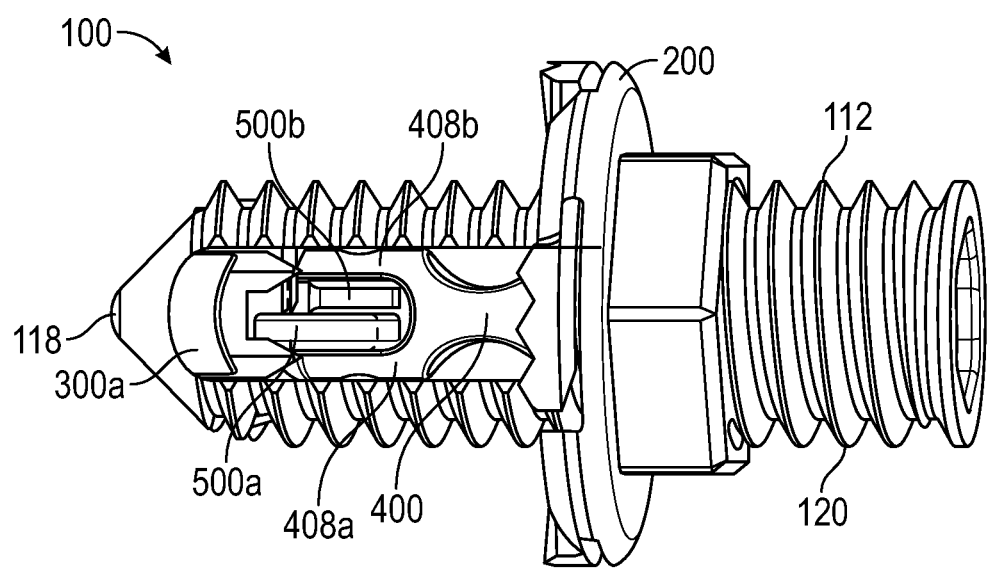
FIG. 7 is another perspective view of the first embodiment of the implant of the invention in an open configuration.

FIG. 7 shows a perspective view of implant 100 in an open configuration, with wing 300a shown in front. As can be seen in FIG. 7, first linkage 500a and second linkage 500b are mounted within the space 409 between arms 408a, 408b of plunger 400.

Figure 8:
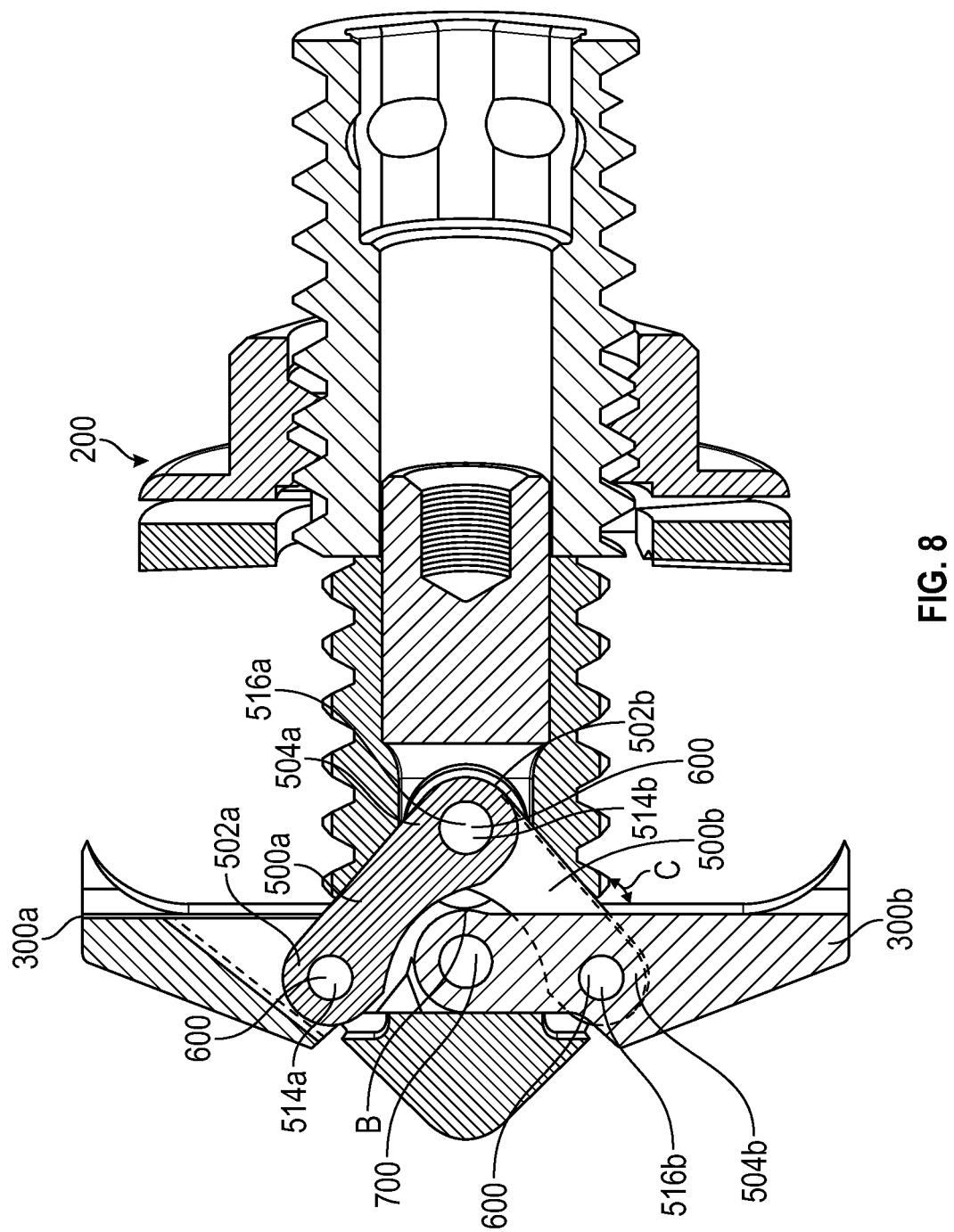
FIG. 8 is a cross-sectional view of the first embodiment of the implant of the invention in the open configuration.

FIG. 8 illustrates a cross-sectional view of implant 100 in an open configuration. As can be seen in FIG. 8, second end 504a of first linkage 500a is connected to first end 502b of second linkage 500b. Planar bottom surface 520a of first linkage 500a is placed in contact with planar top surface 518b of second linkage 500b. As can be seen in FIGS. 2 and 8, a mounting pin 600 is inserted through hole 516a in second end 504a of first linkage 500a, hole 514b in first end 502b of second linkage 500b, hole 414a in first arm 408a of plunger 400, and hole 414b in second arm 408b of plunger 400 to allow for rotation of the linkages 500a, 500b therabout. The opposite ends of linkages 500a, 500b are connected to the wings 300a, 300b to allow for rotation thereof, as will be described further below.

Figure 9A:
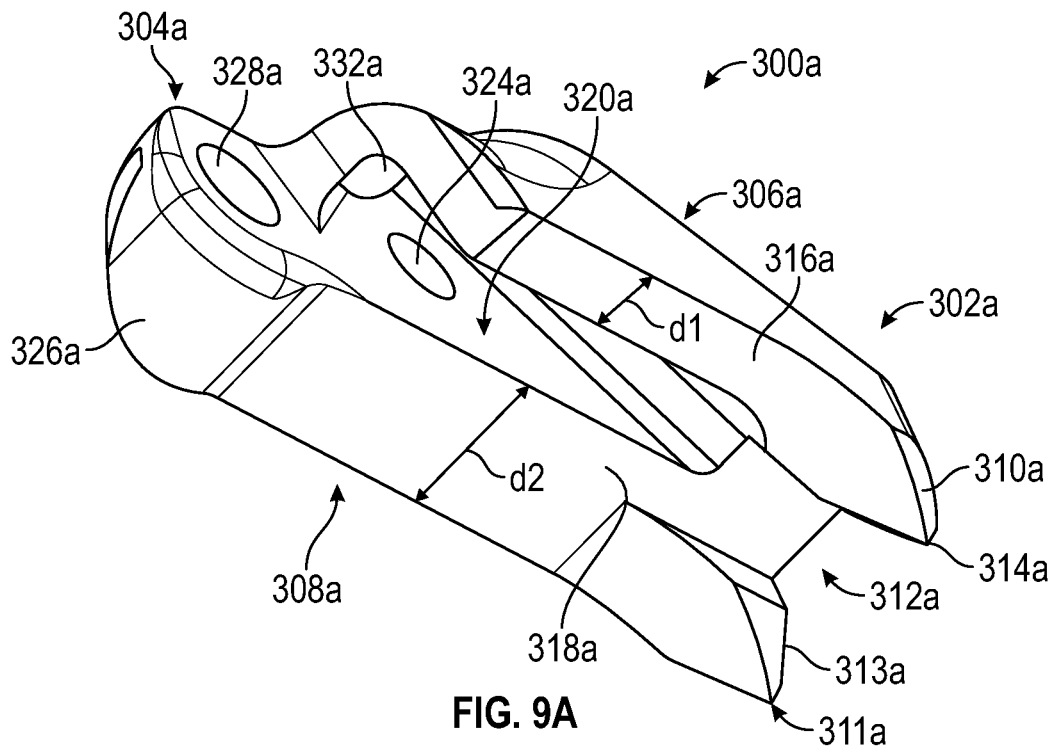
FIG. 9A is a side perspective view of a first embodiment of a first wing of the invention.
Figure 9B:
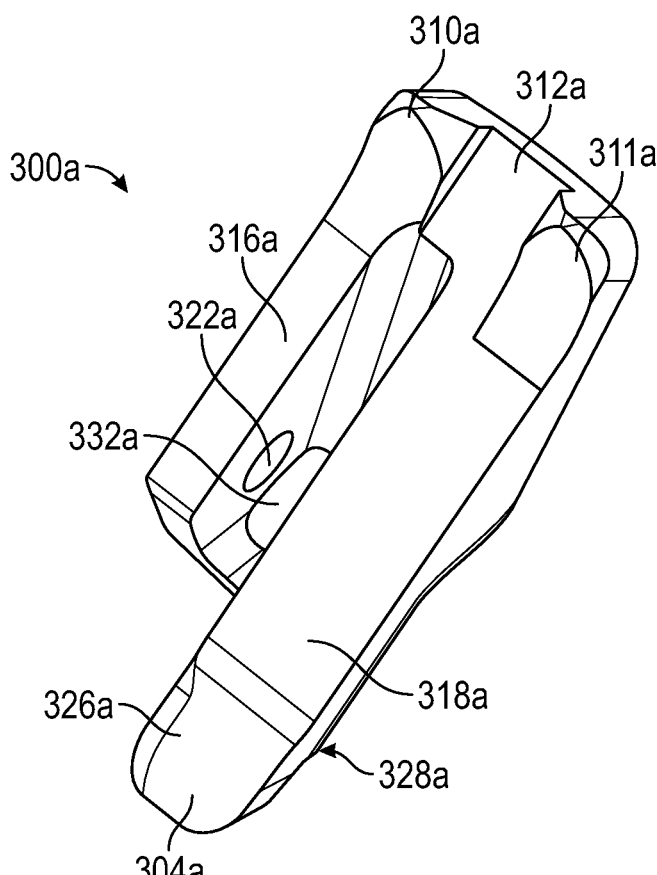
FIG. 9B is a bottom perspective view of the first embodiment of the first wing of the invention.
Figure 9C:
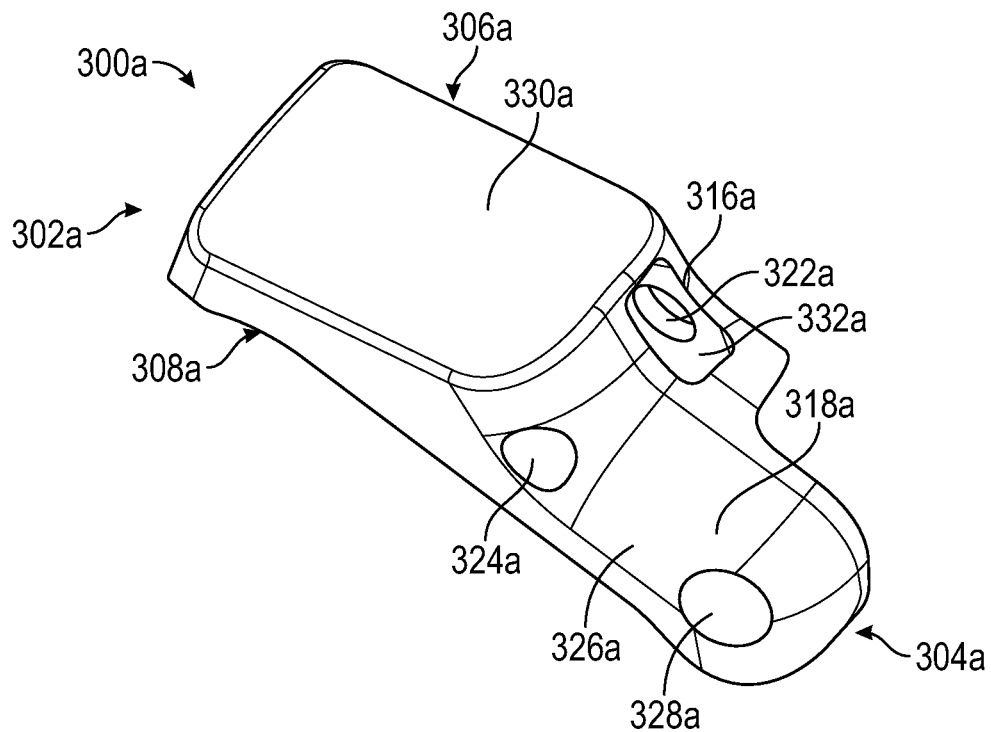
FIG. 9C is a top view of the first embodiment of the first wing of the invention.

FIGS. 9A, 9B, and 9C show perspective views of an embodiment of first wing 300a. Wing 300a has a distal end 302a, a proximal end 304a, a first lateral side 306a, and a second lateral side 308a. In some embodiments, distal end 302a includes at least one fang extending therefrom adapted for engaging bone and/or tissue. In other embodiments, a bottom surface of wing 300a may include a flat roughened surface to achieve gripping of the bone and/or tissue.

In some embodiments, distal end 302a includes first and second fangs 310a, 311a having a gap 312a therebetween. In some embodiments, the dimension of the gap 312a may be about 1.5 mm to about 6 mm. In some embodiments, the gap 312a may be about 3 mm. In some embodiments, first fang 310a has a sharp pointed tip 314a and second fang 311a has a sharp pointed tip 313a. First fang 310a is provided on first lateral side 306a and is connected to first extension 316a. Second fang 311a is provided on second lateral side 308a and is connected to second extension 318a. First extension 316a has a width of d1 and second extension 318a has a width of d2. In some embodiments, width d2 is greater than width d1. In some embodiments, width d1 ranges from about 1.0 mm to about 4.0 mm. In some embodiments, width d2 ranges from about 1.5 mm to about 6.0 mm. A substantially rectangular slot 320a is provided between first extension 316a and second extension 318a for receiving first end 502a of first linkage 500a therein, as can be seen in FIGS. 1, 2 and 7. First extension 316a includes a hole 322a in an inner wall thereof for receiving a pin 600 therein. In some embodiments, hole 322a does not extend fully through the wall of first extension 316a. Second extension 318a includes hole 324a extending therethrough, which is located opposite hole 322a of first extension 316a. A mounting pin 600 is inserted into hole 322a of first extension 316a, hole 514a of first linkage 500a, and hole 324a of second extension 318a to allow for rotation of the wing 300a thereabout.

Wing 300a includes a substantially planar top surface 330a, as can be seen in FIG. 9C. Wing 300a includes a substantially rectangular opening 332a adjacent to top surface 330a. Rectangular opening 332a is adapted to receive first end 502a of first linkage 500a therein in the closed configuration of the wing 300a. Proximal end 304a of wing 300a further includes proximal connector portion 326a having an additional hole 328a for operatively connecting wing 300a to main body 112. Hole 328a is configured to receive a bolt 700 therein.

Figure 10A:
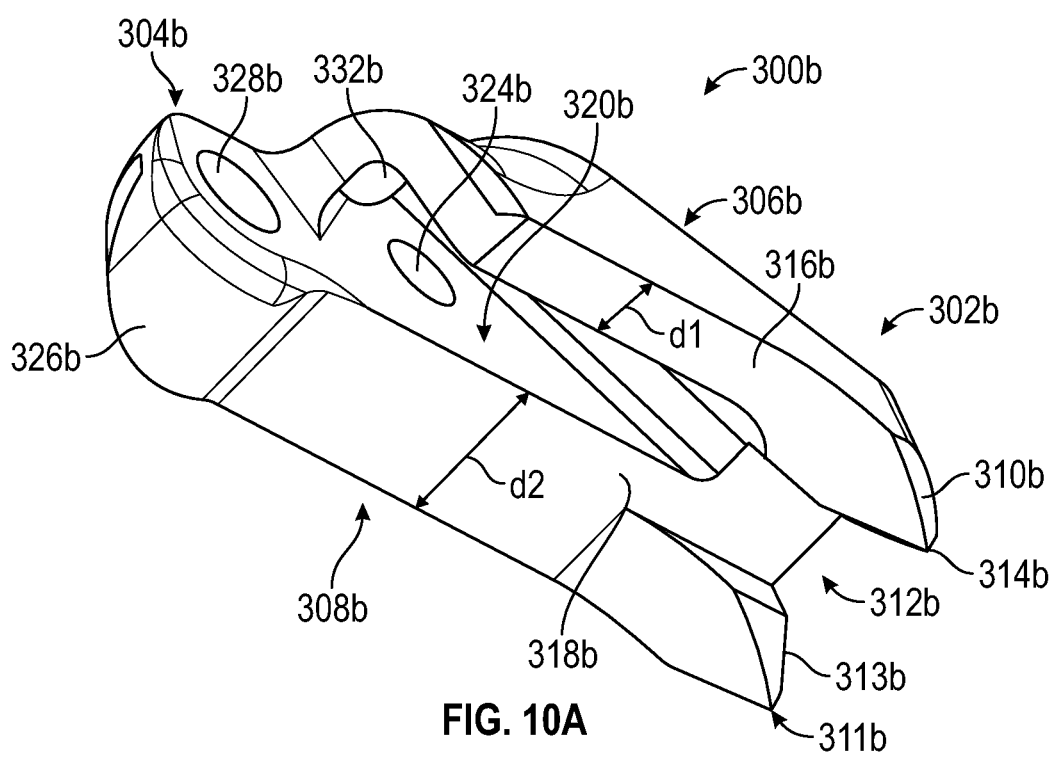
FIG. 10A is a side perspective view of a first embodiment of a second wing of the invention.
Figure 10B:
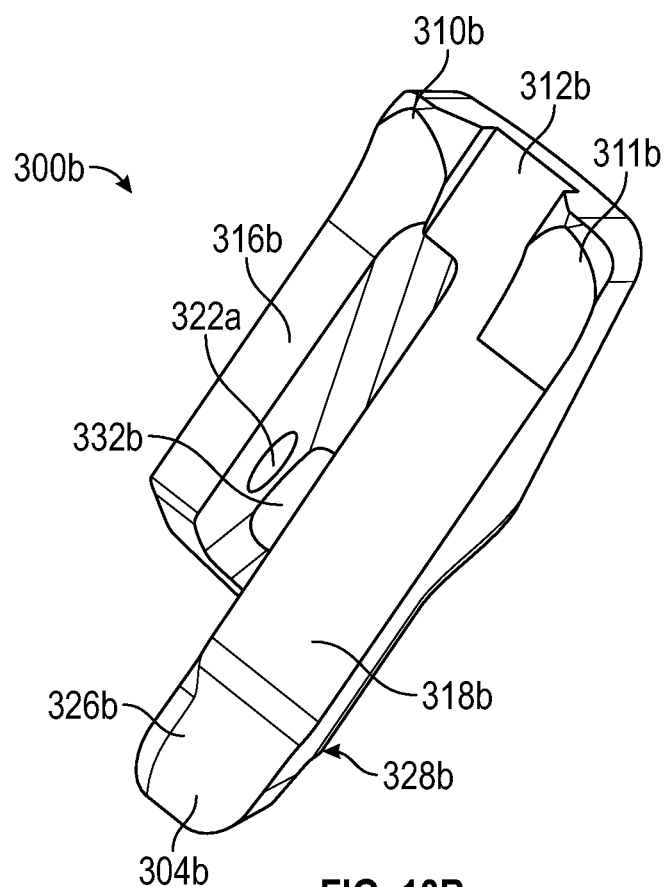
FIG. 10B is a bottom perspective view of the first embodiment of the second wing of the invention.
Figure 10C:
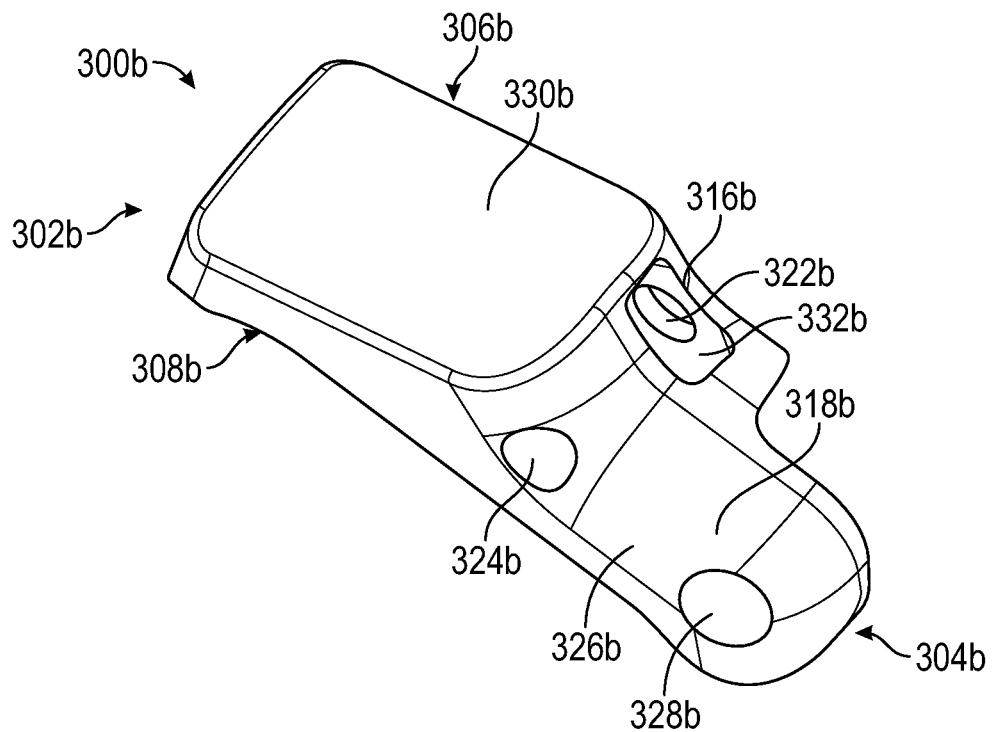
FIG. 10C is a top view of the first embodiment of the second wing of the invention.

FIGS. 10A, 10B, and 10C show perspective views of an embodiment of second wing 300b. Second wing 300b is substantially identical to first wing 300a. Wing 300b has a distal end 302b, a proximal end 304b, a first lateral side 306b, and a second lateral side 308b. In some embodiments, distal end 302b includes at least one fang adapted for engaging bone and/or tissue. In other embodiments, a bottom surface of wing 300b may include a flat roughened surface to achieve gripping of the bone and/or tissue.

In some embodiments, distal end 302b includes first and second fangs 310b, 311b having a gap 312b therebetween. In some embodiments, the dimension of the gap 312b may be about 1.5 mm to about 6 mm. In some embodiments, the gap 312b may be about 3 mm. In some embodiments, first fang 310b has a sharp pointed tip 314b and second fang 311b has a sharp pointed tip 313b. First fang 310b is provided on first lateral side 306b and is connected to first extension 316b. Second fang 311b is provided on second lateral side 308b and is connected to second extension 318b. First extension 316b has a width of d1 and second extension 318b has a width of d2. In some embodiments, width d2 is greater than width d1. A substantially rectangular slot 320b is provided between first extension 316b and second extension 318b for receiving second end 504b of second linkage 500b therein, as can be seen in FIG. 2. First extension 316b includes a hole 322b in an inner wall thereof for receiving a pin 600 therein. Second extension 318b includes hole 324b extending therethrough, which is located opposite hole 322b of first extension 316b. A mounting pin 600 is inserted through hole 322b of first extension 316b, hole 516b of second linkage 500b, and hole 324b of second extension 318b to allow for rotation of the wing 300b thereabout, as can be seen in FIG. 2.

Wing 300b includes a substantially planar top surface 330b, as can be seen in FIG. 10C. Wing 300b includes a substantially rectangular opening 332b adjacent to top surface 330b. Rectangular opening 332b is adapted to receive second end 504b of second linkage 500b therein in the closed configuration of the wing 300b. Proximal end 304b of wing 300b further includes proximal connector portion 326b having an additional hole 328b for operatively connecting wing 300b to main body 112. Hole 328b is configured to receive a bolt 700 therein.

In some embodiments, in the open position, wings 300a, 300b extend circumferentially a distance of about 2 mm to about 15 mm from the main body 112, which may be referred to as the reach, $R_1$, of the wings 300a, 300b. In some embodiments, the spacing of the gap 312a between fangs 310a, 311a may be the same as the spacing of the gap 312b between fangs 310b, 311b. In other embodiments, the spacing of the gap 312a between fangs 310a, 311a may be different from the spacing of the gap 312b between fangs 310b, 311b. The fangs 310a, 311a, 310b, 311b are optimally placed to minimize stress on the spinous process and prevent fracture thereof. The length of any of fangs 310a, 311a, 310b, 311b may be about 0.5 mm to about 5 mm. In some embodiments, each fang can have a different length as desired.

The design of wings 300a, 300b is such that the outer surface acts as a stop relative to main body 112 to control the minimum and maximum movement, thereby preventing closing in on themselves inside the main body 112 and also preventing over-deployment. In some embodiments, the wings 300a, 300b are extended from the main body 112 at an angle C of about 80° to about 90° in the open position. In some embodiments, the wings 300a, 300b are extended from the main body 112 at an angle C of about 90° in the open position.

Figure 11:
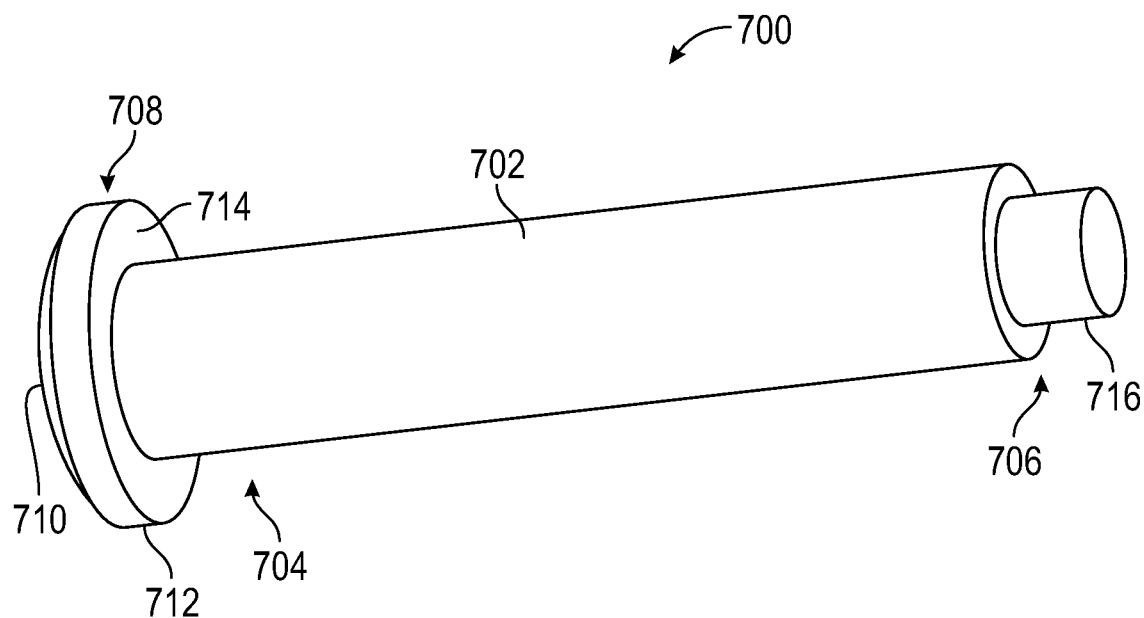
FIG. 11 is a perspective view of a bolt of the invention.
Figure 12:
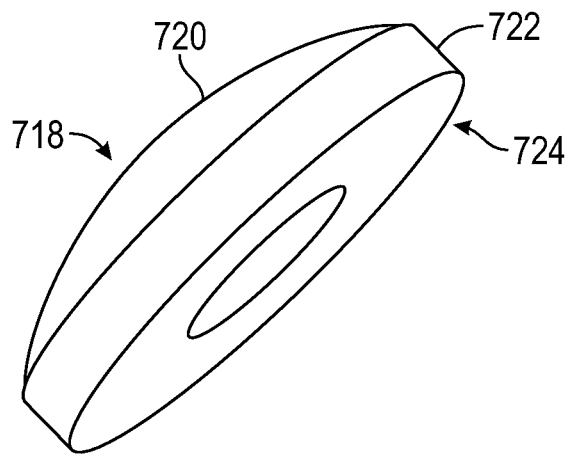
FIG. 12 is a perspective view of a removable head for the bolt of the invention.

FIG. 11 illustrates an embodiment of bolt 700 and FIG. 12 illustrates an embodiment of removable head 718 for connection to bolt 700. Bolt 700 includes a shaft 702 having a proximal end 704 and a distal end 706. Proximal end 704 includes a unitary head 708 having a rounded distal end 710, a side circumferential edge 712, and a flat bottom surface 714. Distal end 706 includes a reduced diameter cylindrical portion 716. Shaft 702 can be inserted through hole 328a of wing 300a, hole 328b of wing 300b, and through openings 138a, 138b of main body 112. Proximal connector portion 326a of wing 300a is thereby adjacent to and connected to proximal connector portion 326b of wing 300b by bolt 700. Shaft 702 has a diameter configured to fit through holes 328a, 328b and to allow the wings 300a, 300b to freely rotate thereabout. Once bolt 700 is inserted through main body 112 and wings 300a, 300b, a removable head 718 may be connected to cylindrical portion 716 to hold the bolt 700 securely in place. The head 718 may be connected by any mechanical fastening means. As shown in FIG. 12, an embodiment of removable head 718 is shaped similarly to unitary head 708, having a rounded distal end 720, a side circumferential edge 722, and a flat bottom surface 724. Head 718 and head 708 are set within the openings 138a, 138b such that the distal ends 710, 720 are recessed and do not extend circumferentially beyond the helical threads 120, as seen in FIG. 4.

Figure 13:
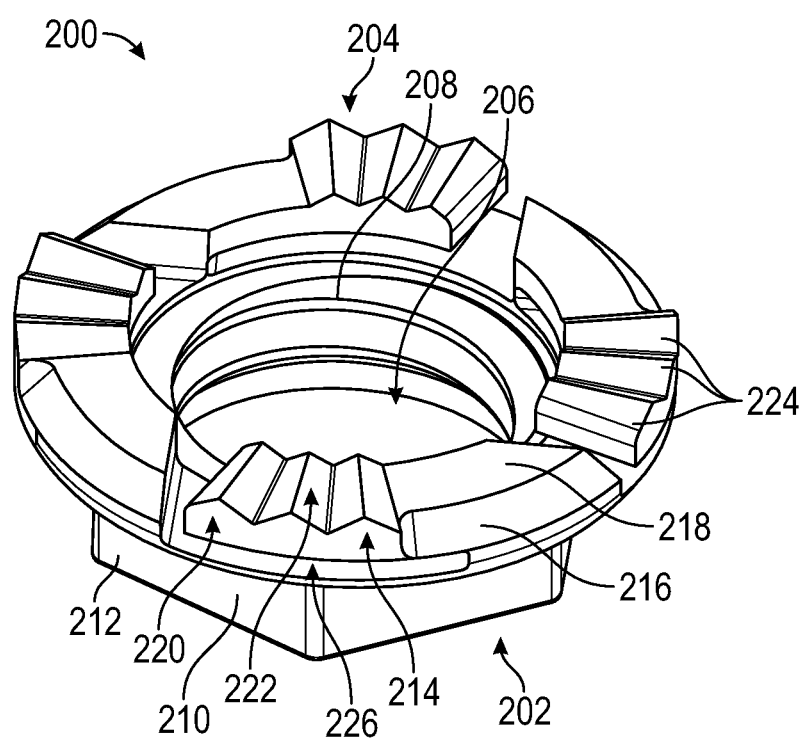
FIG. 13 is a perspective view of an embodiment of a nut of the invention.

FIG. 13 illustrates an embodiment of nut 200. Nut 200 can be provided on the proximal end 116 of main body 112. Nut 200 has a proximal side 202, a distal side 204, and an internal bore 206 therethrough. In some embodiments, internal bore 206 has interior helical threads 208 for cooperating with helical threads 120 on the exterior surface of main body 112. In operation, the nut 200 can be rotated to move the nut longitudinally along the shaft of main body 112 such that the distal side 204 engages tissue and/or bone. In some embodiments, proximal side 202 has a hexagonal extension 210 with flat sides 212. In some embodiments, distal side 204 forms a grip plate having a plurality of flex arms 214. In one embodiment, the grip plate includes four flex arms 214. In other embodiments, the grip plate may include two flex arms, three flex arms, or five or more flex arms.

In some embodiments, each flex arm 214 may have a fixed portion 216 with a smooth top surface 218 and a movable portion 220 with a textured top surface 222. The movable portion 220 may have a space 226 therebelow. The textured top surface 222 is configured to engage bone or tissue when the implant is placed in the body to help anchor the implant 100 in place. The movable portion 220 is configured to flex into open space 226 when the implant 100 is engaged with tissue and/or bone. In some embodiments, the movable portion 220 may flex proximally an amount of from about 1 degree to about 50 degrees. In some embodiments, the movable portion 220 may flex proximally an amount of from about 1 degree to about 10 degrees. In some embodiments, the textured top surface 222 may include teeth, spikes, or any other type of mechanical gripping surface. In one embodiment, the textured top surface 222 may include three substantially triangular shaped teeth 224. In other embodiments, the distal side 204 has a unitary circumferential roughened or textured surface without any flex arms. The nut 200 extends circumferentially a distance of about 2 mm to about 15 mm from the main body 112. In some embodiments, the nut 200 extends circumferentially a distance of about 2 mm to about 8 mm. This reach allows for sufficient bone fixation while ensuring that the implant 100 can be easily inserted through a standard tissue dilation sleeve/tube.

The present invention may provide a posterior fixation device intended for use in the non-cervical spine (T1-S1). The implant is intended for plate fixation/attachment to the spinous process for achieving fusion for lumbar spinal stenosis, degenerative disc disease, spondylolisthesis, trauma, and/or tumors. The implant may be inserted via a minimally invasive lateral approach (L1-S1) or a minimally invasive posterior approach (T1-S1). In some embodiments, the implant may be used with bone graft material.

For a spinal implant procedure, a patient may be placed in a prone position on a frame to decrease the lordosis of the spine and avoid compression of the abdomen. The surgeon may tilt the pelvis by inclining the surgical table at the level of the pelvis, allowing for natural distraction of the spinous processes. Using a lateral minimally invasive surgical (MIS) approach, an incision may be made, and a guide wire may be introduced into the patient's body, which may be done using an aiming device under fluoroscopy. The guidewire is then advanced between the spinous processes and pierces the interspinous ligament. Once the guidewire is advanced as desired, which may be approximately 2 cm across the midline of the spine, the aiming device may be removed with the guidewire remaining in place. A guidewire extension may be placed on the proximal end of the guidewire to help maintain guidewire placement during the procedure. A series of blunt dilators may then be placed over the guidewire to create a pathway to the spinous processes, which are then removed with the guidewire remaining in place.

A graduated bone tap may then be inserted over the guidewire. Bone tap may be used to distract the spinous processes, remove the interspinous ligament, and partially decorticate the spinous processes for stimulating bone growth. Bone tap may be rotated clockwise to gradually decorticate and/or to distract the spinous processes. The bone tap may be threaded into the interspinous process space such that the threads are engaged with the spinous processes and tap a path for the implant to be inserted along. Once adequate distraction is obtained, the degree of distraction can be determined by viewing the bone tap's sizing holes under fluoroscopy. This degree of distraction thereby determines the appropriate implant size, which may be an 8 mm, 10 mm, 12 mm, 14 mm, or 16 mm implant. The bone tap and the guidewire can then be removed, and the spinal implant can be placed. Before the implant is inserted into the patient, bone graft material is added. Specifically, bone graft material may be added by opening the wings and adding bone graft material into the lumen of the threaded body. Bone graft material may also be applied around the exterior threads of the implant.

Figure 14:
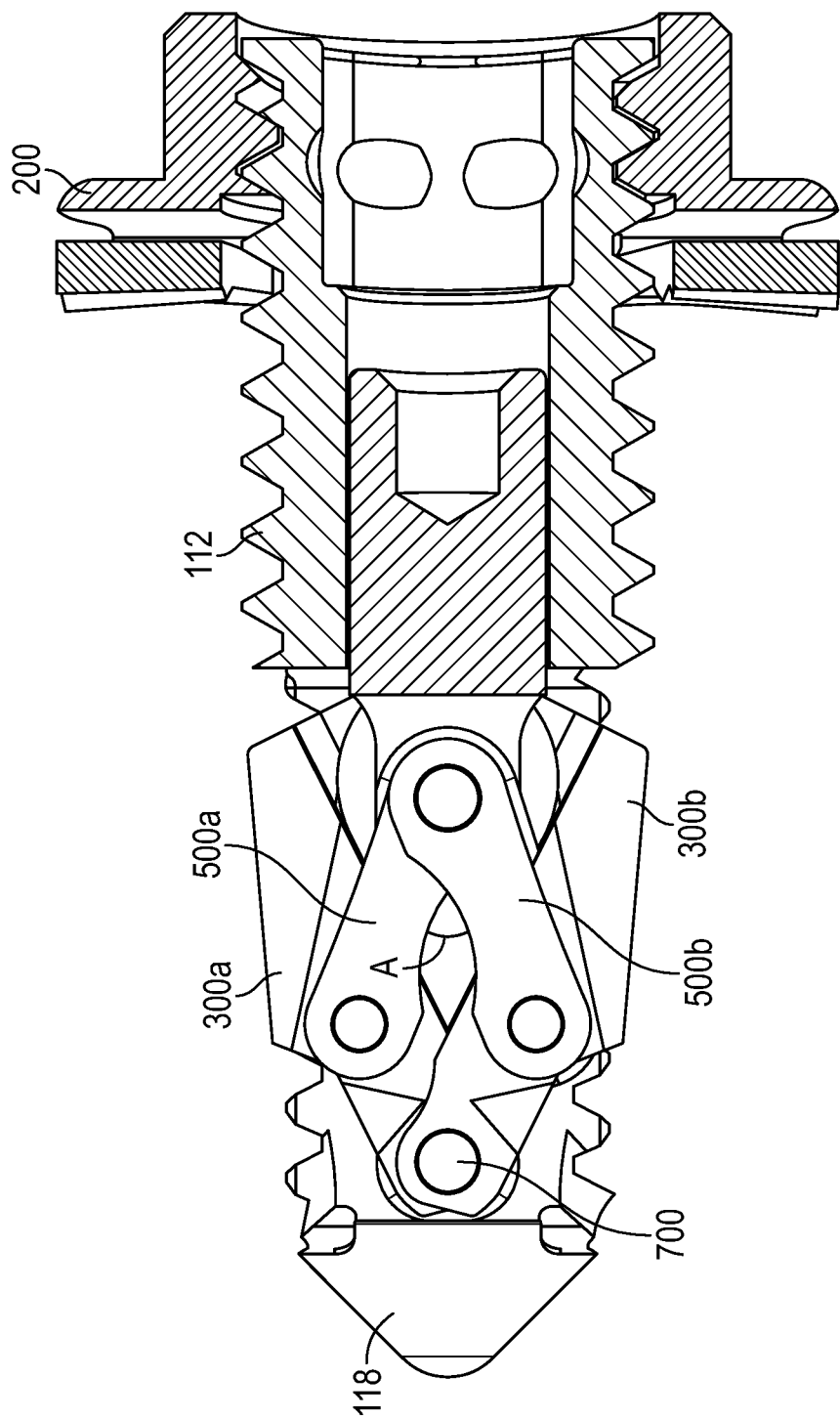
FIG. 14 is a cross-sectional view of the first embodiment of the implant of the invention in the closed configuration.

The implant 100 may be inserted using an inserter device (not shown) into the body of a patient in the closed configuration, as shown in FIGS. 4, 14 and 15. With respect to FIGS. 14 and 15, the plunger 400 is in a proximal position, such that the first and second linkages 500a, 500b form a first angle A therebetween and the wings 300a, 300b are in a closed configuration. Once the implant 100 is inserted into the desired location in the patient's body, the wings 300a, 300b can be moved to an open configuration, as shown in FIGS. 1, 2, 7 and 8. The plunger 400 may be moved distally such that the ends 502a, 504b of the linkages 500a, 500b, respectively, are caused to separate forming a second angle B therebetween, shown in FIG. 8. Angle B is greater than angle A. In some embodiments, angle A is about 35° and angle B is about 85°. As the linkages 500a, 500b separate, the wings 300a, 300b rotate around pins 600 and bolt 700 into an open configuration.

Figure 16:
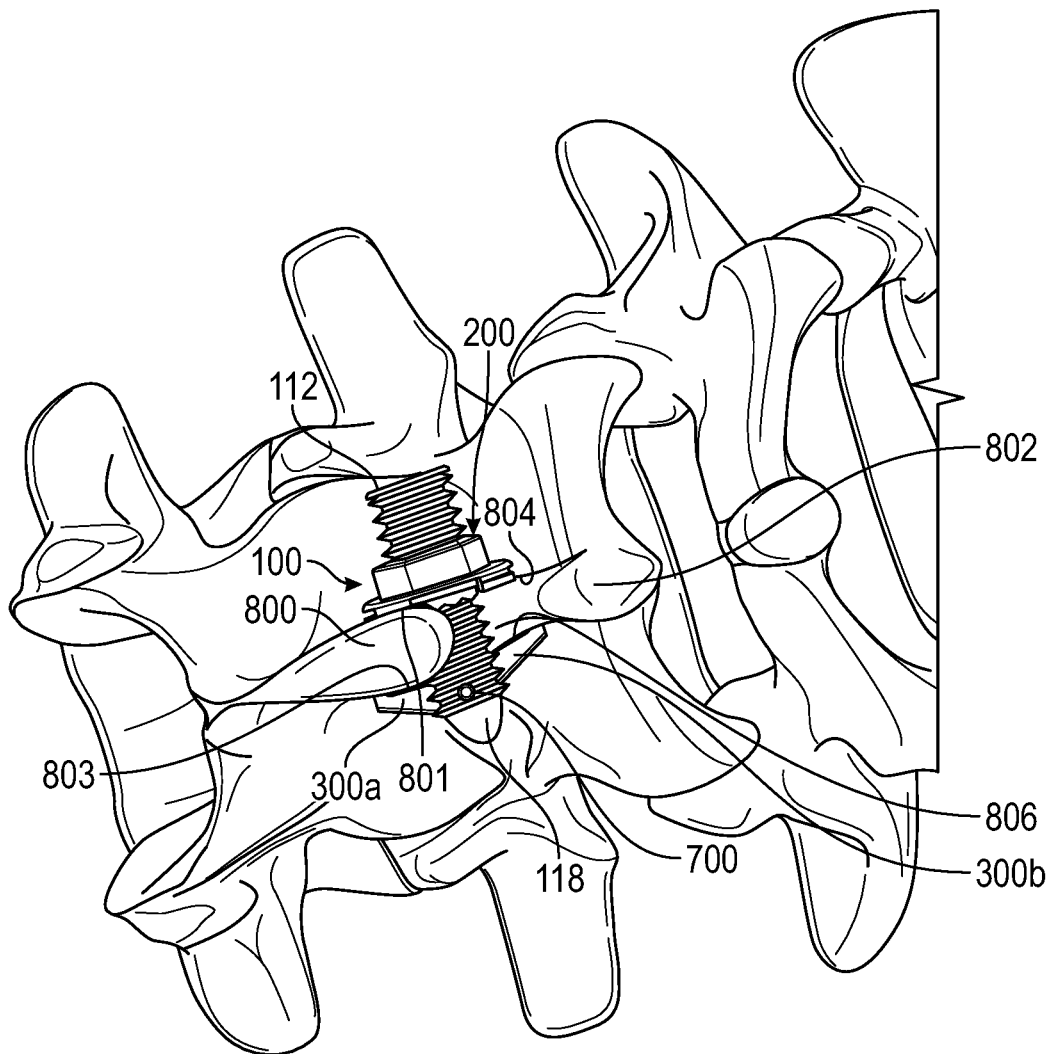
FIG. 16 is a view of the first embodiment of the implant of the invention implanted in the spine of a patient.

The implant may then be moved proximally to engage the wings 300a, 300b with the bone and/or tissue at the implant site, as can be seen in FIG. 16. The nut 200 may then be moved distally, such as by rotation, to engage the bone and/or tissue as well forming a proximal anchor. Specifically, nut 200 engages a first lateral surface 801 of a first spinous process 800 and a second lateral surface 804 of a second spinous process 802. In some embodiments, the flex arms 214 may be flexed proximally when the nut 200 is tightly engaged with bone and/or tissue at the implant site. Additionally, wings 300a, 300b engage a third opposite surface 803 of first spinous process 800 and a fourth opposite surface 806 of second spinous process 802. Specifically, the fangs 310a, 311a, 310b, 311b of wings 300a, 300b may engage with the bone and/or tissue at the implant site forming a distal anchor. In some embodiments, the wings 300a, 300b and the nut 200 can be engaged on opposite sides of the spinal process when the implant 100 is in place, as seen in FIG. 16.

Second Embodiment

Figure 17:
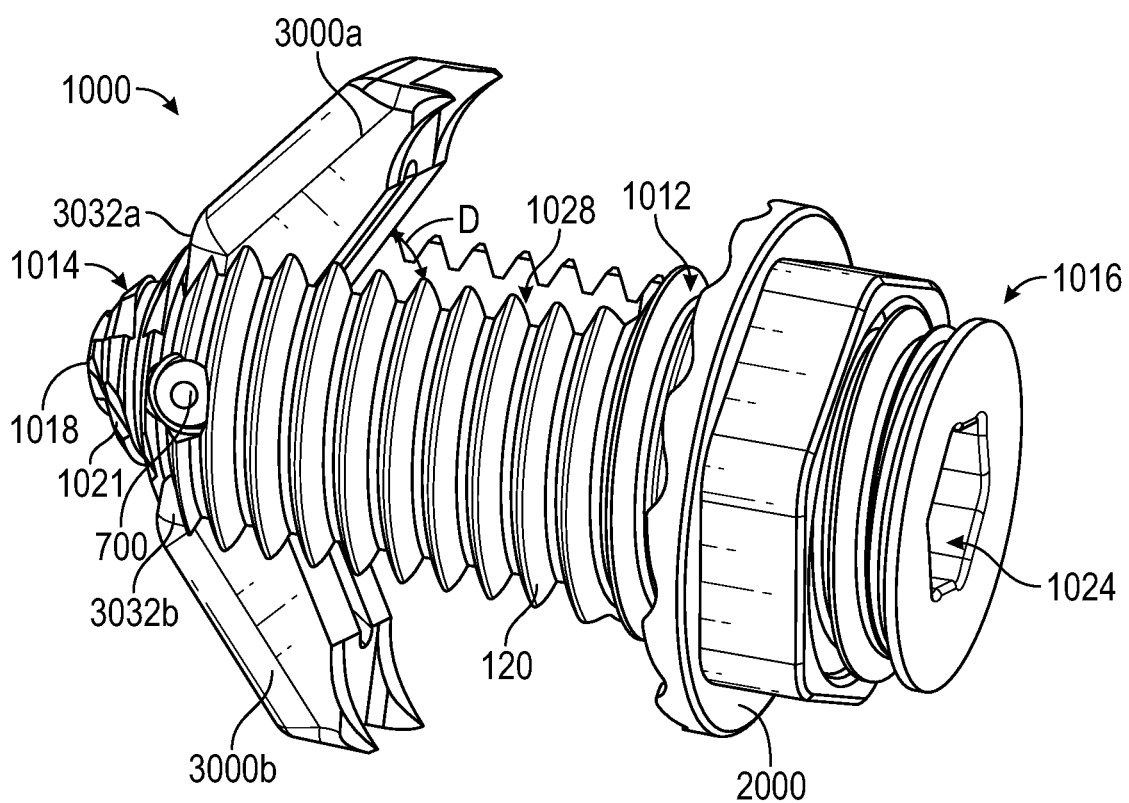
FIG. 17 is a perspective view of a second embodiment of the implant of the invention in an open configuration.

Another embodiment of the invention is shown in FIGS. 17-25, which illustrates an interspinous process implant 1000. FIG. 17 illustrates implant 1000 in an open configuration. Implant 1000 may include a main body 1012 having a distal end 1014 and a proximal end 1016. Implant 1000 further includes a nut 2000 on the proximal end 1016 of main body 1012 and extendable first and second wings 3000*a*, 3000*b* on the distal end 1014 of main body 1012. As can be seen in the cross-sectional view of FIG. 18, implant 1000 further includes a plunger 4000 and first and second linkages 5000*a*, 5000*b* for operatively connecting first and second wings 3000*a*, 3000*b* to main body 1012, as will be described herein.

As can be seen in FIG. 17, distal end 1014 of main body 1012 includes a conical distal tip 1018 having a rounded distalmost end. In some embodiments, the conical distal tip has a sharp pointed distalmost end. In some embodiments, main body 1012 includes helical threads 120 on an exterior surface thereof. In some embodiments, main body 1012 may alternatively or additionally include cutting threads or box threads. Helical threads 120 may be provided along the entire exterior surface of main body 1012 or along only a portion of the exterior surface of main body 1012. In some embodiments, the threads may have a depth of about 0.5 to about 3.0 mm, an angle of about 45° to about 100°, and a spacing of about 1.0 mm to about 4.0 mm. In some embodiments, the threads may have a depth of about 1.0 mm, an angle of about 60°, and a spacing of about 1.75 mm. In some embodiments, distal tip 1018 includes cutting threads 1021 to aid in inserting the implant 1000 into the bone (see FIG. 24C). In some embodiments, distal tip 1018 has a smooth exterior surface without any threads thereon. In some embodiments, the distal tip 1018 is a solid tip for providing strength during insertion of the implant 100.

Main body 1012 further includes a proximal portion 1022 extending from the proximal end 1016, having hollow bore 1024. The majority of hollow bore 1024 may be substantially cylindrical. Proximal end of hollow bore 1024 may have a particular shape such as a hexagonal perimeter configured to receive an insertion tool therein (not shown). Proximal end of hollow bore 1024 may also include detents 1025 adapted for receiving and locking a distal end of an insertion tool therein (not shown).

Main body 1012 also includes a distal portion 1026 extending from the distal end 1014, having a substantially rectangular window 1028. The window 1028 extends from a first lateral side to a second lateral side, and has a top flat interior wall, and a bottom flat interior wall, similar to main body 112 as shown in FIG. 3. At the distal end of the window 1028, top wall and bottom wall include an opening therethrough configured to receive a bolt 700 for mounting wings 3000*a*, 3000*b*, as seen in FIG. 17.

Figure 23:
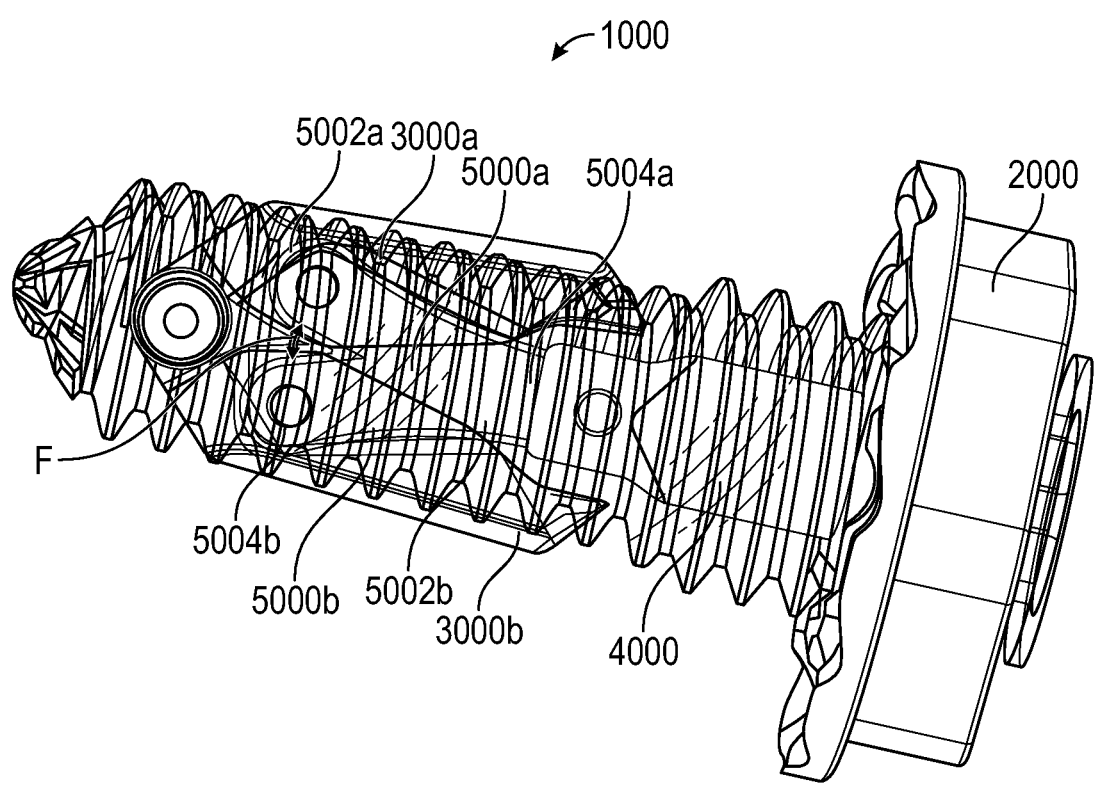
FIG. 23 is a perspective view of the second embodiment of the implant of the invention in a closed configuration.

FIG. 23 illustrates implant 1000 with wings 3000*a*, 3000*b* in a closed configuration. Window 1028 of main body 1012 is configured to house a distal portion of the plunger 4000, first and second linkages 5000*a*, 5000*b*, and first and second wings 3000*a*, 3000*b* when in the closed configuration.

Figure 18:
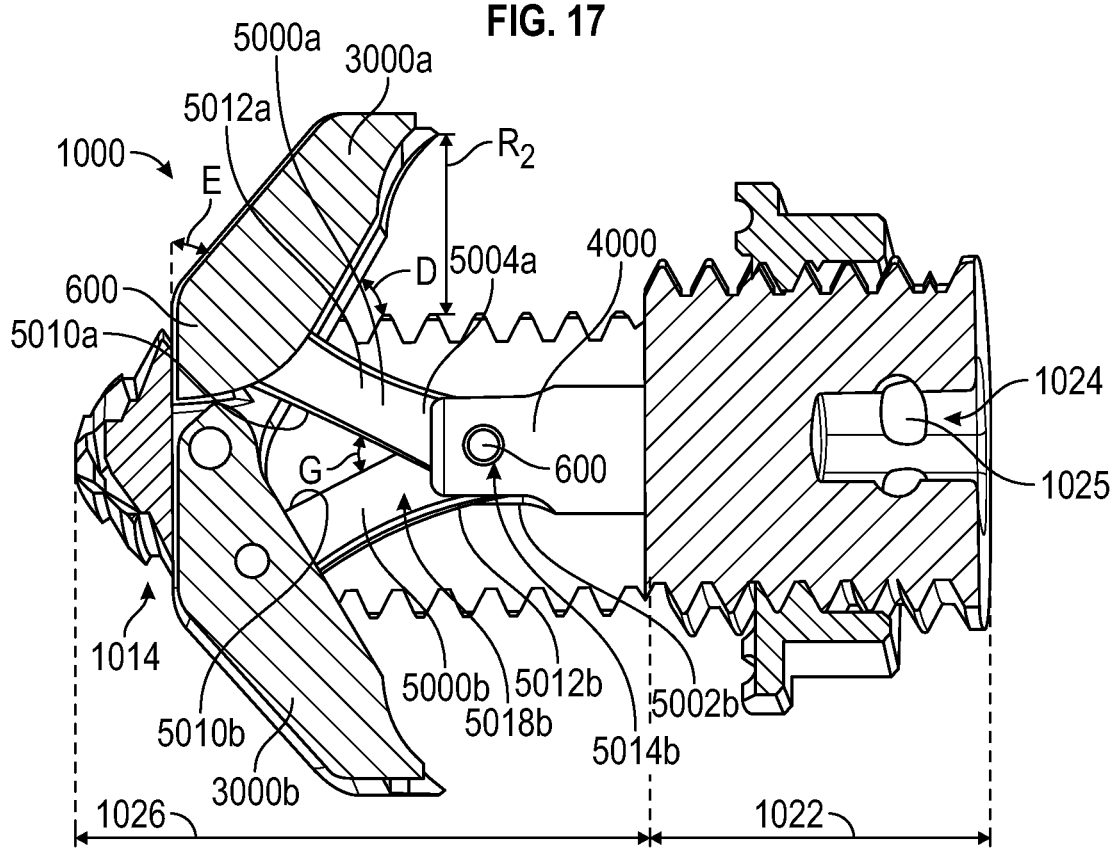
FIG. 18 is a cross-sectional view of the second embodiment of the implant of the invention in an open configuration.
Figure 19:
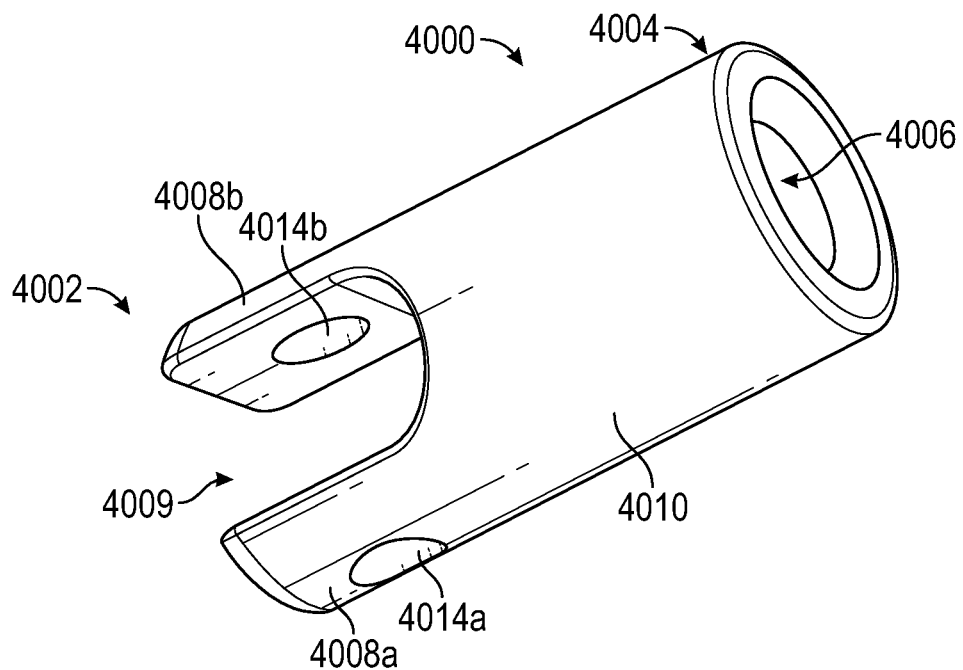
FIG. 19 is a perspective view of a second embodiment of a plunger of the invention.

FIG. 19 illustrates a second embodiment of plunger 4000. Plunger 4000 has a distal end 4002 and proximal end 4004. Proximal end 4004 is configured to be located within the bore 1024 of main body 1012 and distal end 4002 is configured to be located within the window 1028 of the main body 112, as seen in FIGS. 18 and 23. Plunger 4000 can be moved longitudinally within the bore 1024 and window 1028 to open and close the wings 3000*a*, 3000*b*, as will be described further below.

With respect to FIG. 19, proximal end 4004 of plunger 4000 has a central bore 4006 for receiving an inserter device (not shown) therein. In some embodiments, central bore 4006 of plunger 4000 may be threaded to cooperate with threading on an inserter device. Plunger 4000 has a substantially Y-shaped construction, having a first arm 4008*a* and a second arm 4008*b* extending from a solid central portion 4010. First arm 4008*a* and second arm 4008*b* have a space 4009 therebetween. Central portion 4010 has a substantially cylindrical configuration, as can be seen in FIG. 19. Plunger 4000 does not have indentations like the embodiment of plunger 400 (which can hold bone graft material) because the plunger 4000 is located more proximally than plunger 400 when the wings 3000*a*, 3000*b* are in the open position. Thus, plunger 4000 is not configured to extend longitudinally into the window 1028 as far as plunger 400 does. First arm 4008*a* and second arm 4008*b* each have a hole 4014*a*, 4014*b* extending therethrough for receiving mounting pin 600 therein. In order to connect wings 3000*a*, 3000*b* to the plunger 4000, linkages 5000*a*, 5000*b* are mounted within the space 4009 between the arms 4008*a*, 4008*b*. In some embodiments, plunger 4000 may have a total length of about 9 mm to about 11 mm. In some embodiments, plunger 4000 may have a total length of about 10.4 mm. In some embodiments, first and second arms 4008*a*, 4008*b* may have a length of about 4-5 mm. In some embodiments, first and second arms 4008*a*, 4008*b* may have a length of about 4.5 mm.

Figure 20:
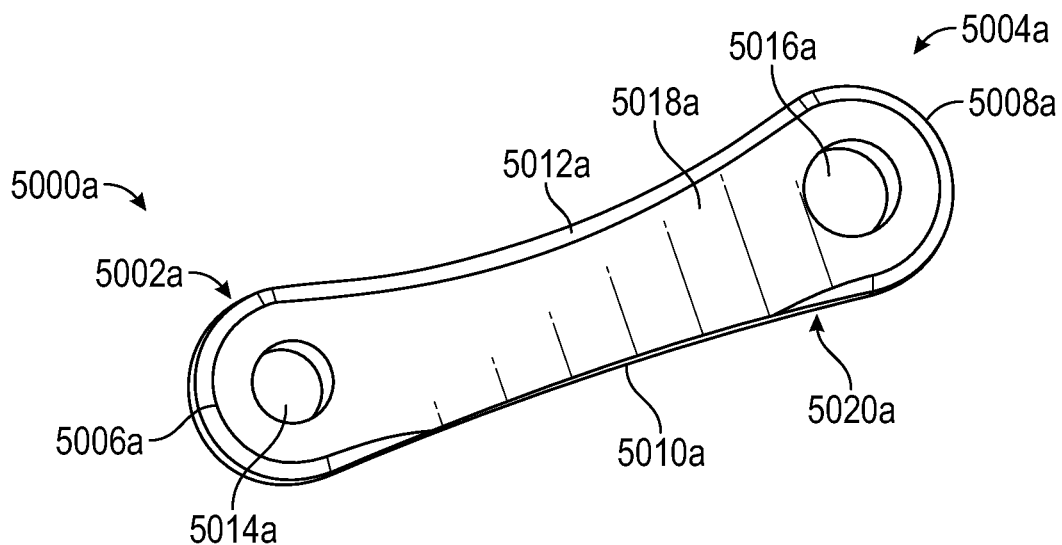
FIG. 20 is a perspective view of a second embodiment of a first linkage of the invention.

FIG. 20 illustrates an embodiment of first linkage 5000*a*. First linkage 5000*a* has a first end 5002*a* and a second end 5004*a*. In some embodiments, first linkage 5000*a* is substantially oval shaped with first end 5002*a* having a rounded edge 5006*a*, and second end 5004*a* having a rounded edge 5008*a*. First linkage 5000*a* further includes a straight bottom edge 5010*a* and a curved top edge 5012*a*. First end 5002*a* includes a hole 5014*a* extending therethrough and second end 5004*a* includes a hole 5016*a* extending therethrough. Holes 5014*a* and 5016*a* are each configured to receive mounting pin 600 therein. First linkage 5000*a* includes a substantially planar top surface 5018*a* and a substantially planar bottom surface 5020*a*.

Second linkage 5000*b* is substantially identical to first linkage 5000*a*, including a straight bottom edge 5010*b* and a curved top edge 5012*b*. In some embodiments, first and second linkages 5000*a*, 5000*b* may have a length of about 12 mm to 14 mm. In some embodiments, first and second linkages 5000*a*, 5000*b* may have a length of about 13.0 mm. In some embodiments, the distance between the holes 5014*a* and 5016*a* may be about 9 mm to about 11 mm. The distance between the holes 5014*a* and 5016*a* may be about 9.75 mm. Curved top edges 5012*a*, 5012*b* may have a curvature with a radius of about 15.0 mm.

FIG. 18 illustrates a cross-sectional view of implant 1000 in an open configuration. As can be seen in FIG. 18, second end 5004*a* of first linkage 5000*a* is connected to first end 5002*b* of second linkage 5000*b*. Planar bottom surface 5020*a* of first linkage 5000*a* is placed in contact with planar top surface 5018*b* of second linkage 5000*b*. As can be seen in FIG. 18, a mounting pin 600 is inserted through hole 5016*a* in second end 5004*a* of first linkage 5000*a*, hole 5014*b* in first end 5002*b* of second linkage 5000*b*, hole 4014*a* in first arm 4008*a* of plunger 4000, and hole 4014*b* in second arm 4008*b* of plunger 4000 to allow for rotation of the linkages 5000*a*, 5000*b* thereabout. The opposite ends of linkages 5000*a*, 5000*b* are connected to the wings 3000*a*, 3000*b* to allow for rotation thereof, as will be described further below.

Figure 21A:
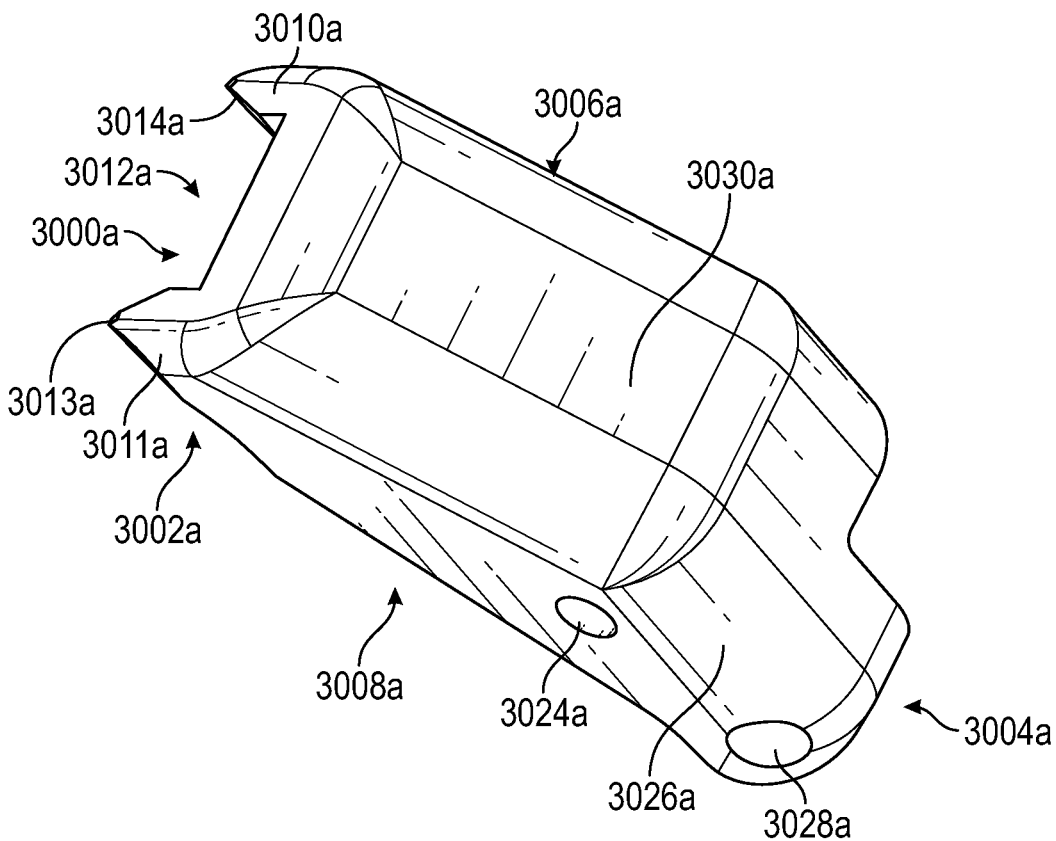
FIG. 21A is a top perspective view of a second embodiment of a first wing of the invention.
Figure 21B:
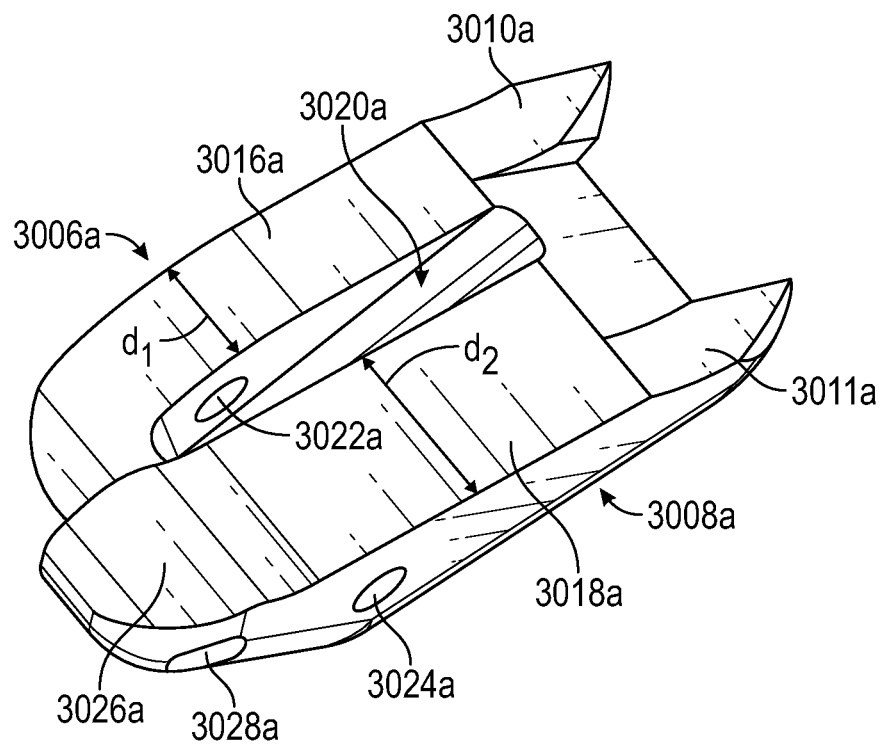
FIG. 21B is a bottom perspective view of the second embodiment of a first wing of the invention.
Figure 21C:
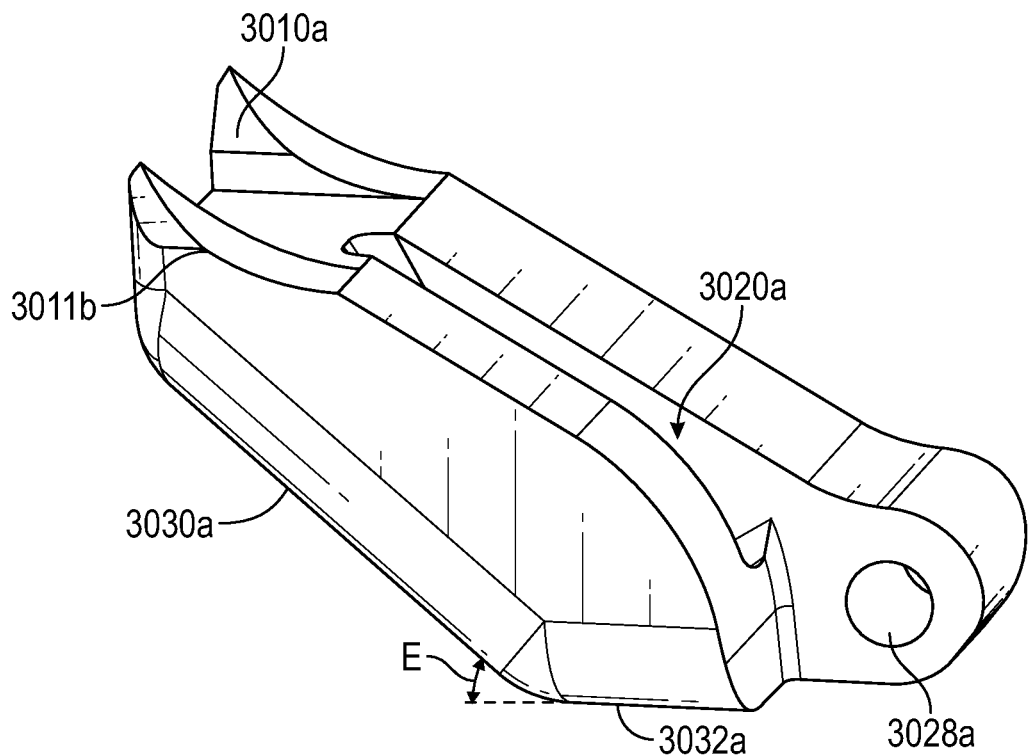
FIG. 21C is a side perspective view of the second embodiment of a first wing of the invention.

FIGS. 21A, 21B, and 21C show perspective views of an embodiment of first wing 3000*a*. Wing 3000*a* has a distal end 3002*a*, a proximal end 3004*a*, a first lateral side 3006*a*, and a second lateral side 3008*a*. In some embodiments, distal end 3002*a* includes at least one fang extending therefrom adapted for engaging bone and/or tissue. In other embodiments, a bottom surface of wing 3000a may include a flat roughened surface to achieve gripping of the bone and/or tissue.

Figure 22:
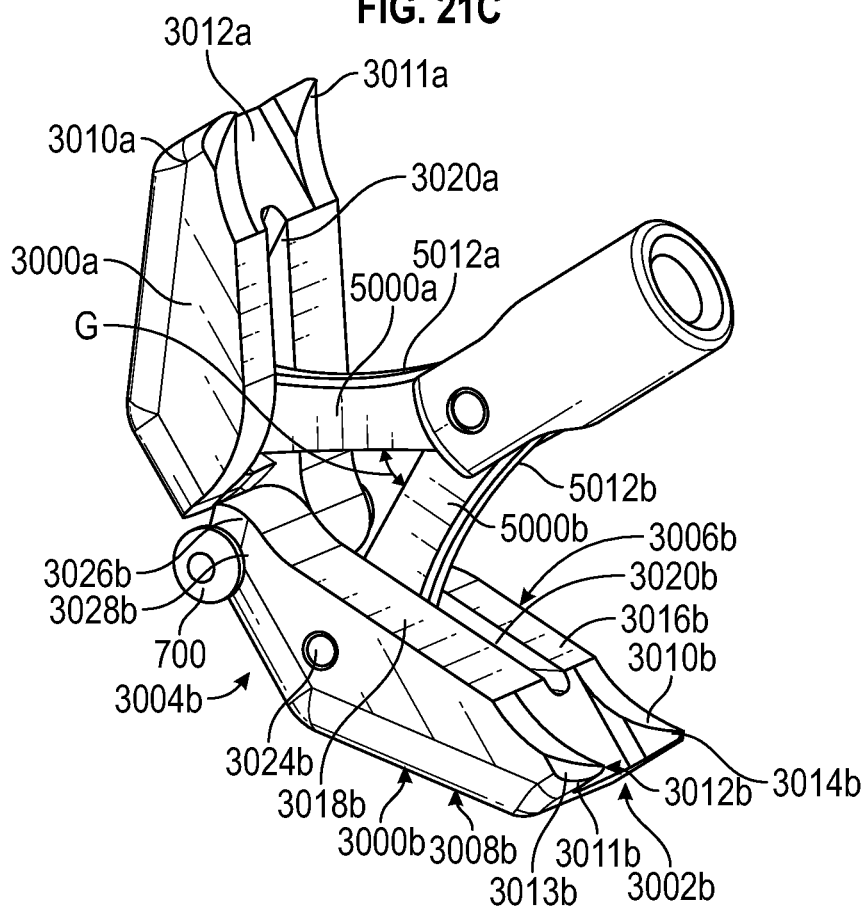
FIG. 22 is a perspective internal view of the second embodiment of the first and second wings, the first and second linkages, and the plunger of the invention, with the main body hidden.

In some embodiments, distal end 3002a includes first and second fangs 3010a, 3011a having a gap 3012a therebetween. In some embodiments, the dimension of the gap 3012a may be about 1.5 mm to about 6 mm. In some embodiments, the gap 3012a may be about 3 mm. In some embodiments, first fang 3010a has a sharp pointed tip 3014a and second fang 3011a has a sharp pointed tip 3013a. First fang 3010a is provided on first lateral side 3006a and is connected to first extension 3016a. Second fang 3011a is provided on second lateral side 3008a and is connected to second extension 3018a. First extension 3016a has a width of d1 and second extension 3018a has a width of d2. In some embodiments, width d2 is greater than width d1. In some embodiments, width d1 ranges from about 1.0 mm to about 4.0 mm. In some embodiments, width d1 ranges from about 1.0 mm to about 2.2 mm. In some embodiments, width d2 ranges from about 1.5 mm to about 6.0 mm. In some embodiments, width d2 ranges from about 2.3 mm to about 3.6 mm. A substantially rectangular slot 3020a is provided between first extension 3016a and second extension 3018a for receiving first end 5002a of first linkage 5000a therein, as can be seen in FIGS. 18 and 22. First extension 3016a includes a hole 3022a in an inner wall thereof for receiving pin 600 therein. In some embodiments, hole 3022a does not extend fully through the wall of first extension 3016a. Second extension 3018a includes hole 3024a extending therethrough, which is located opposite hole 3022a of first extension 3016a. A mounting pin 600 is inserted into hole 3022a of first extension 3016a, hole 5014a of first linkage 5000a, and hole 3024a of second extension 3018a to allow for rotation of the wing 3000a thereabout.

Wing 3000a includes a substantially planar top surface 3030a and a base surface 3032a, as can be seen in FIG. 21A. Top surface 3030a extends at an angle E relative to base surface 3032a. In some embodiments, angle E is about 35° to about 45°. In some embodiments, angle E is about 41°. Wing 3000a does not include any opening adjacent to top surface 3030a, like wing 300a does. Due to the angled design of the wing 3000a, such an opening is not necessary. Proximal end 3004a of wing 3000a further includes proximal connector portion 3026a having an additional hole 3028a for operatively connecting wing 3000a to main body 1012. Hole 3028a is configured to receive bolt 700 therein.

Second wing 3000b is substantially identical to first wing 3000a. Wing 3000b has a distal end 3002b, a proximal end 3004b, a first lateral side 3006b, and a second lateral side 3008b. In some embodiments, distal end 3002b includes at least one fang adapted for engaging bone and/or tissue. In other embodiments, a bottom surface of wing 3000b may include a flat roughened surface to achieve gripping of the bone and/or tissue.

In some embodiments, distal end 3002b includes first and second fangs 3010b, 3011b having a gap 3012b therebetween. In some embodiments, the dimension of the gap 3012b may be about 1.5 mm to about 6 mm. In some embodiments, the gap 3012b may be about 3 mm. In some embodiments, first fang 3010b has a sharp pointed tip 3014b and second fang 3011b has a sharp pointed tip 3013b. First fang 3010b is provided on first lateral side 3006b and is connected to first extension 3016b. Second fang 3011b is provided on second lateral side 3008b and is connected to second extension 3018b. First extension 3016b has a width of d1 and second extension 3018b has a width of d2. In some embodiments, width d2 is greater than width d1. A substantially rectangular slot 3020b is provided between first extension 3016b and second extension 3018b for receiving second end 5004b of second linkage 5000b therein, as can be seen in FIG. 22. First extension 3016b includes a hole in an inner wall thereof for receiving a pin 600 therein. Second extension 3018b includes hole 3024b extending therethrough, which is located opposite the hole of first extension 3016b. A mounting pin 600 is inserted through hole of first extension 3016b, hole 5016b of second linkage 5000b, and hole 3024b of second extension 3018b to allow for rotation of the wing 3000b thereabout, as can be seen in FIG. 22. FIG. 22 illustrates the wings 3000a, 3000b, first and second linkages 5000a, 5000b, and plunger 4000, but does not show main body 1012 in order to better view the internal linkages.

Wing 3000b includes a substantially planar top surface, similar to wing 3000a, as seen in FIG. 21A. Proximal end 3004b of wing 3000b further includes proximal connector portion 3026b having an additional hole 3028b for operatively connecting wing 3000b to main body 1012. Hole 3028b is configured to receive a bolt 700 therein, as seen in FIG. 22.

In some embodiments, in the open position, wings 3000a, 3000b extend circumferentially a distance of about 2 mm to about 15 mm from the main body 1012, which may be referred to as the reach, $R_2$, of the wings 3000a, 3000b. In some embodiments, the spacing of the gap 3012a between fangs 3010a, 3011a may be the same as the spacing of the gap 3012b between fangs 3010b, 3011b. In other embodiments, the spacing of the gap 3012a between fangs 3010a, 3011a may be different from the spacing of the gap 3012b between fangs 3010b, 3011b. The fangs 3010a, 3011a, 3010b, 3011b are optimally placed to minimize stress on the spinous process and prevent fracture thereof. The length of any of fangs 3010a, 3011a, 3010b, 3011b may be about 0.5 mm to about 5 mm. In some embodiments, each fang can have a different length as desired.

As seen in FIGS. 17-18, the design of wings 3000a, 3000b is such that the base surface 3032a, 3032b acts as a stop relative to main body 1012 to control the minimum and maximum movement, thereby preventing closing in on themselves inside the main body 1012 and also preventing over-deployment. In some embodiments, the wings 3000a, 3000b are extended from the main body 1012 at an angle D of about 50° to about 70° in the open position. In some embodiments, the wings 3000a, 3000b are extended from the main body 1012 at an angle D of about 60° in the open position.

Figure 24A:
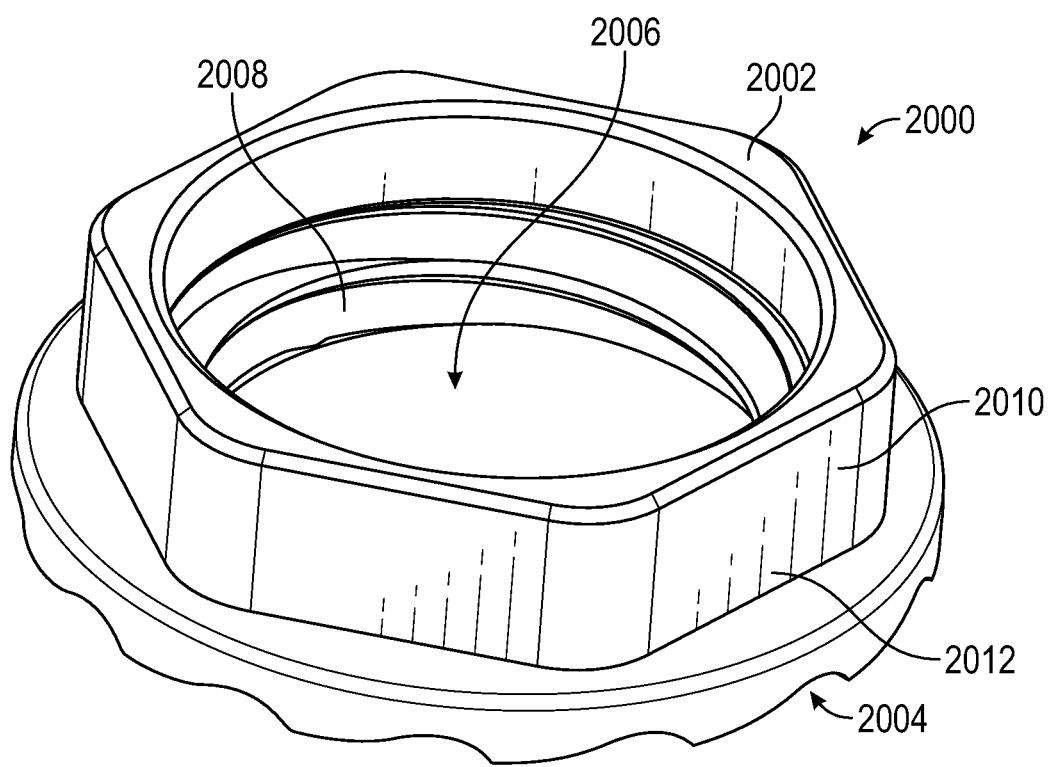
FIG. 24A is a side perspective view of a second embodiment of a nut of the invention.
Figure 24B:
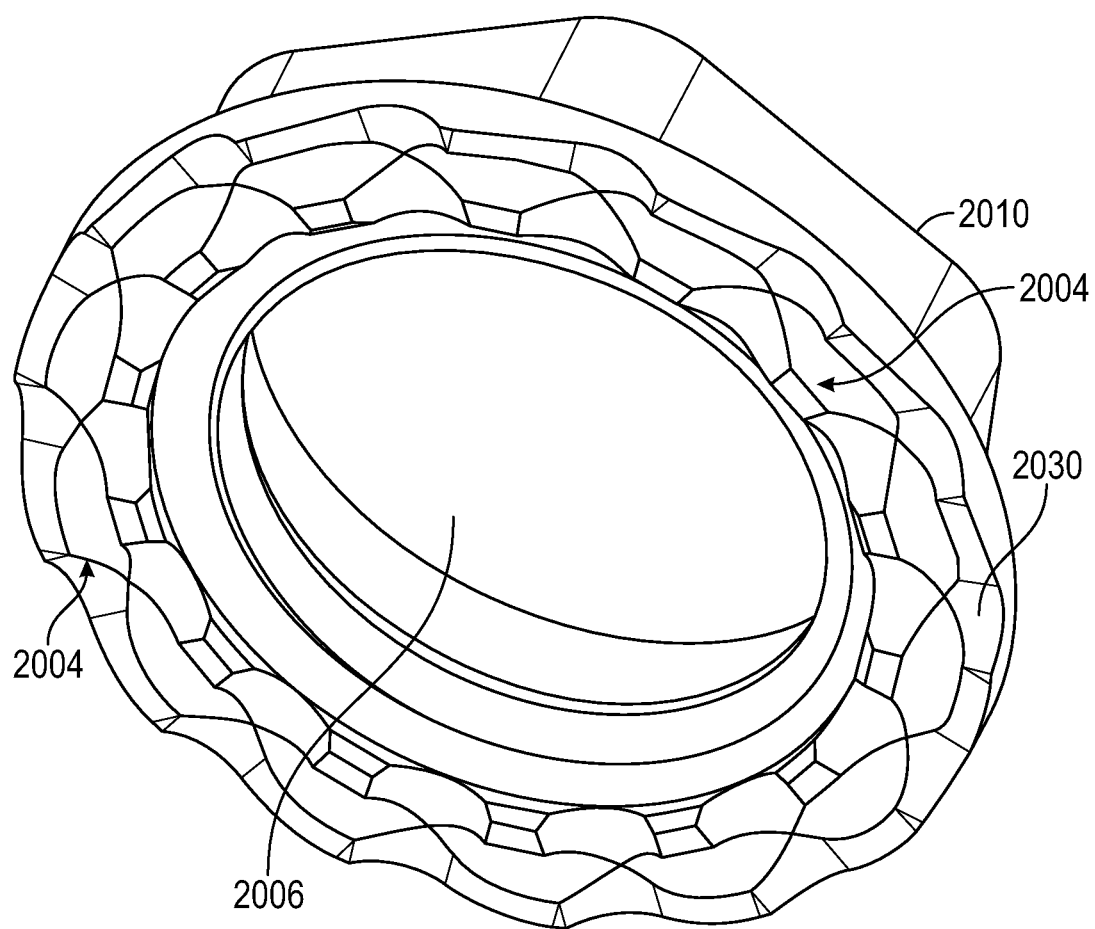
FIG. 24B is a bottom perspective view of the second embodiment of a nut of the invention.
Figure 24C:
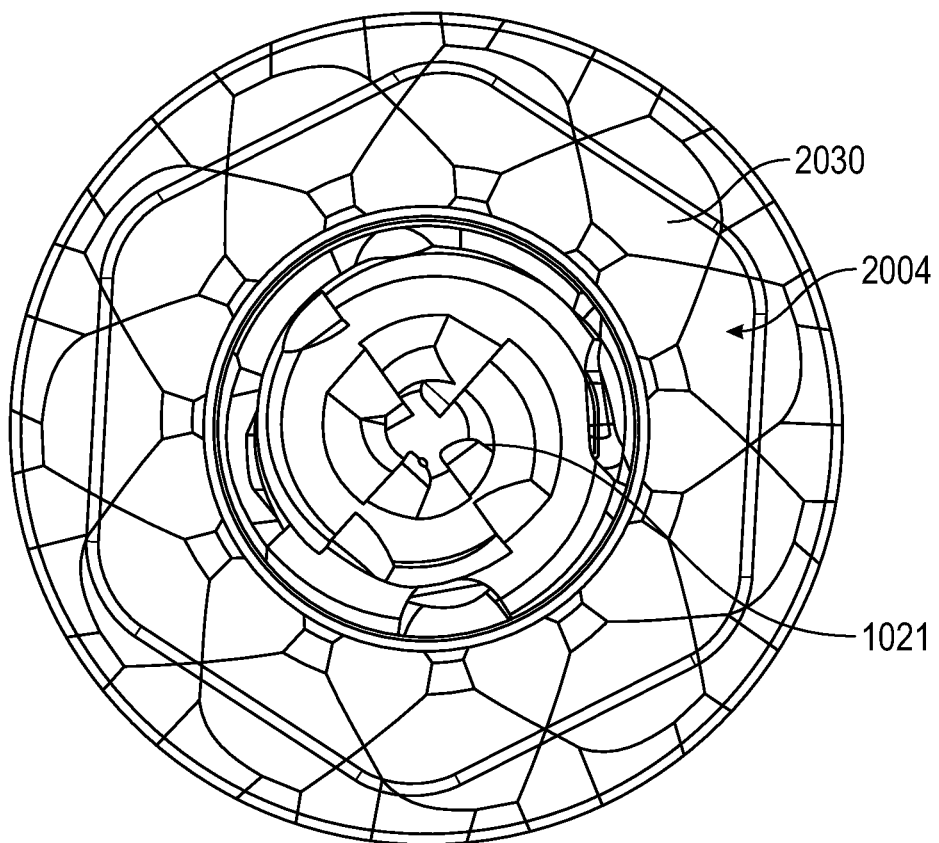
FIG. 24C is a bottom end view of the second embodiment of a nut of the invention.

FIGS. 24A, 24B, 24C illustrate an embodiment of nut 2000. Nut 2000 can be provided on the proximal end 1016 of main body 1012. Nut 2000 has a proximal side 2002, a distal side 2004, and an internal bore 2006 therethrough. In some embodiments, internal bore 2006 has interior helical threads 2008 for cooperating with helical threads 120 on the exterior surface of main body 1012. In operation, the nut 2000 can be rotated to move the nut longitudinally along the shaft of main body 1012 such that the distal side 2004 engages tissue and/or bone. In some embodiments, proximal side 2002 has a hexagonal extension 2010 with flat sides 2012.

Figure 25:
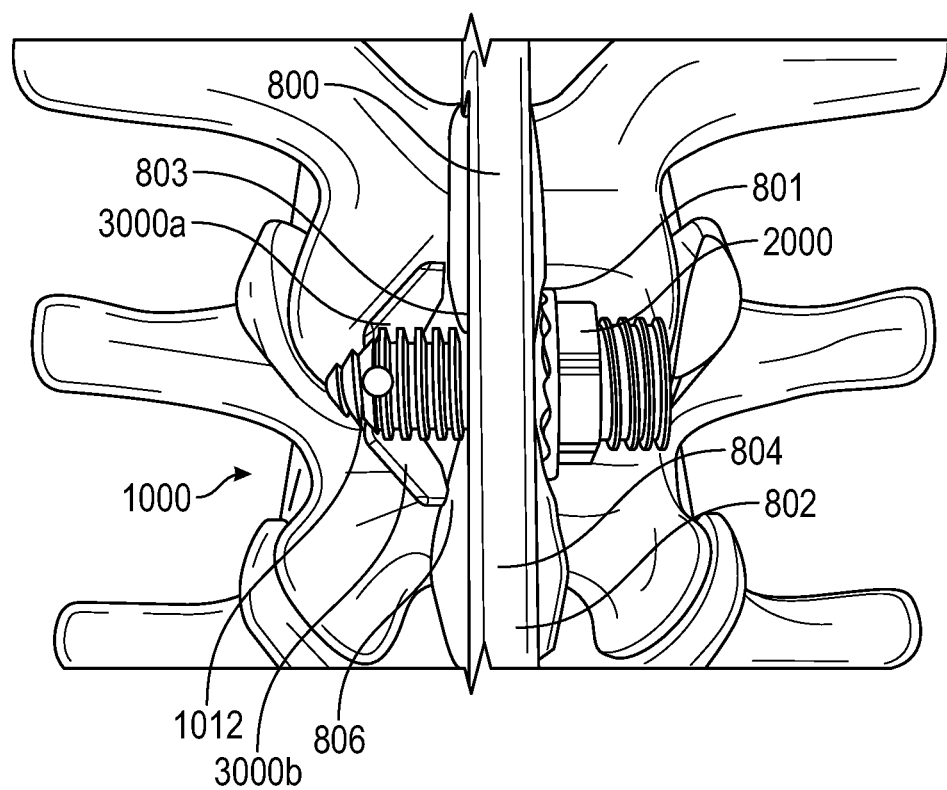
FIG. 25 is a view of the second embodiment of the implant of the invention implanted in the spine of a patient.

In some embodiments, distal side 2004 forms a grip plate having a textured surface 2030. Textured surface 2030 may be configured to engage bone or tissue when the implant 1000 is placed in the body to help anchor the implant 1000 in place, as seen in FIG. 25. In some embodiments, the textured surface 2030 may include bumps, crenelations, teeth, spikes, or any other type of mechanical gripping surface. The nut 2000 extends circumferentially a distance of about 2 mm to about 15 mm from the main body 1012. In some embodiments, the nut 2000 extends circumferentially a distance of about 2 mm to about 8 mm. This reach allows for sufficient bone fixation while ensuring that the implant 1000 can be easily inserted through a standard tissue dilation sleeve/tube. In some embodiments, nut 2000 can be provided in two sizes—a first size for implants of 8 mm, 10 mm, and 12 mm; and a second size for implants of 14 mm and 16 mm.

The implant 1000 may be inserted using an inserter device (not shown) into the body of a patient in the closed configuration, as shown in FIG. 23. With respect to FIG. 23, the plunger 4000 is in a proximal position, such that the first and second linkages 5000a, 5000b form a first angle F therebetween and the wings 3000a, 3000b are in a closed configuration. Once the implant 1000 is inserted into the desired location in the patient's body, the wings 3000a, 3000b can be moved to an open configuration, as shown in FIGS. 17, 18 and 22. The plunger 4000 may be moved distally such that the ends 5002a, 5004b of the linkages 5000a, 5000b, respectively, are caused to separate forming a second angle G therebetween, shown in FIGS. 18 and 22. Angle G is greater than angle F. In some embodiments, angle F is about 25° and angle G is about 45°. As the linkages 5000a, 5000b separate, the wings 3000a, 3000b rotate around pins 600 and bolt 700 into an open configuration.

The implant may then be moved proximally to engage the wings 3000a, 3000b with the bone and/or tissue at the implant site, as can be seen in FIG. 25. The nut 2000 may then be moved distally, such as by rotation, to engage the bone and/or tissue as well forming a proximal anchor. Specifically, nut 2000 engages a first lateral surface 801 of a first spinous process 800 and a second lateral surface 804 of a second spinous process 802. Additionally, wings 3000a, 3000b engage a third opposite surface 803 of first spinous process 800 and a fourth opposite surface 806 of second spinous process 802. Specifically, the fangs 3010a, 3011a, 3010b, 3011b of wings 3000a, 3000b may engage with the bone and/or tissue at the implant site forming a distal anchor. In some embodiments, the wings 3000a, 3000b and the nut 2000 can be engaged on opposite sides of the spinal process when the implant 1000 is in place, as seen in FIG. 25.

The implant 100, 1000 may be provided in different selected sizes to properly fit into the desired space of a particular patient. The implant body diameter may provide for a range of about 6-20 mm spinous process space distraction. In some embodiments, the diameter of the main body 112, 1012 may be about 8 mm, about 10 mm, about 12 mm, about 14 mm, or about 16 mm. The sizes of the implant may be color-coded to allow the surgeon to easily identify the size of the implant and match the implant with a properly sized insertion tool (not shown), which may have similar size color-coding.

In some embodiments, all or part of the implant may be composed of titanium or a titanium alloy. In other embodiments, all or part of the implant may be composed of stainless steel. In some embodiments, all or part of the implant may be composed of a polymer or a bioabsorbable material. In some embodiments, the implant may be manufactured by an additive manufacturing process. In some embodiments, the implant may be manufactured by machining or molding. In some embodiments, all or part of the implant may include a coating on at least one surface thereof. In some embodiments, at least one outer surface of the implant may be coated with hydroxyapatite (HA). In some embodiments, multiple surfaces may be coated with HA.

In some embodiments, the implant 100, 1000 may have a total length of about 30 mm to 45 mm. In some embodiments, the implant 100, 1000 may have a total length of about 32 mm to about 34 mm. In some embodiments, the implant 100 may have a total length of about 33 mm. In some embodiments, the implant 1000 may have a total length of about 34 mm.

In some embodiments, main body 112, 1012 may be adapted to contain bone graft material therein. The bone graft material may be added to the implant 100, 1000 by holding wing 300a, 3000a open and holding wing 300b, 3000b closed and injecting bone graft material into the main body 112, 1012 (or vice versa). Bone graft material may also be applied around the exterior helical threads 120 before insertion of the implant 100, 1000 into the body. In some embodiments, the bone graft material may be viscous to avoid any interference with the proper functioning of the wings 300a, 3000a, 300b, 3000b. The volume of the bone graft material may range from about 0.5 cc to about 3.0 cc, or from about 1.2 cc to about 2.5 cc, depending on the size of the implant 100.

Features described above as well as those claimed below may be combined in various ways without departing from the scope hereof. The following examples illustrate some possible, non-limiting combinations:

(A1) A spinal implant comprising: a main body having a central bore and a longitudinal axis extending between a proximal end and a distal end; a proximal anchor including a nut received on an outer surface of the main body; a distal anchor having a first closed configuration and a second open configuration, the distal anchor including: a first wing having a first inner end and a first outer end, and a second wing having a second inner end and a second outer end, wherein the first inner end is rotatably connected to the second inner end at a first pivot point; and an internal plunger having a proximal end and a distal end, the internal plunger housed within the central bore of the main body, the distal end of the internal plunger connected to both a proximal end of a first linkage and a proximal end of a second linkage at a second pivot point, wherein longitudinal distal movement of the internal plunger rotates the first outer end of the first wing and the second outer end of the second wing distally to transition from the first closed configuration to the second open configuration, and longitudinal proximal movement of the internal plunger folds the first wing and the second wing proximally to transition from the second open configuration to the first closed configuration.

(A2) For the spinal implant denoted as (A1), wherein a distal end of the first linkage is connected to the first wing at a third pivot point near the first inner end, and a distal end of the second linkage is connected to the second wing at a fourth pivot point near the second inner end.

(A3) For the spinal implant denoted as (A1) or (A2), wherein the first wing and the second wing form an angle of about 60 degrees with respect to the main body in the second open configuration.

(A4) For the spinal implant denoted as any of (A1) or (A2), wherein the first wing and the second wing form an angle of about 80 degrees to about 90 degrees with respect to the main body in the second open configuration.

(A5) For the spinal implant denoted as any of (A1) through (A4), wherein the distal end of the internal plunger includes: a first arm, a second arm, and a space between the first arm and the second arm, wherein a proximal end of the first linkage and a proximal end of the second linkage are mounted in the space between the first arm and the second arm of the internal plunger.

(A6) For the spinal implant denoted as any of (A1) through (A5), wherein the first linkage and the second linkage are substantially identical.

(A7) For the spinal implant denoted as any of (A1) through (A6), wherein the first wing includes a substantially planar top surface and a base surface at the first inner end, the top surface extending at an angle of about 35 to about 45 degrees relative to the base surface.

(A8) For the spinal implant denoted as any of (A1) through (A7), wherein the second wing includes a substantially planar top surface and a base surface at the second inner end, the top surface extending at an angle of about 35 to about 45 degrees relative to the base surface.

(A9) For the spinal implant denoted as any of (A1) through (A8), wherein the first linkage and the second linkage form an angle of about 45 degrees in the second open configuration.

(A10) For the spinal implant denoted as any of (A1) through (A9), wherein the first linkage and the second linkage form an angle of about 25 degrees in the first closed configuration.

(A11) For the spinal implant denoted as any of (A1) through (A8), wherein the first linkage and the second linkage form an angle of about 85 degrees in the second open configuration.

(A12) For the spinal implant denoted as any of (A1) through (A11), wherein the first wing includes a first slot on an inner surface for receiving the first linkage therein, and the second wing includes a second slot on an inner surface for receiving the second linkage therein.

(A13) For the spinal implant denoted as any of (A1) through (A12), wherein at least one of the first outer end of the first wing includes at least one pointed protrusion adapted to engage tissue or bone or the second outer end of the second wing includes at least one pointed protrusion adapted to engage tissue or bone.

(A14) For the spinal implant denoted as any of (A1) through (A13), wherein a distal side of the nut includes a textured surface adapted to engage tissue or bone.

(B1) A method of placing a spinal implant at a treatment site comprising: providing a spinal implant in a first closed configuration, the spinal implant including: a main body having a central bore and a longitudinal axis extending between a proximal end and a distal end; a proximal anchor including a nut received on an outer surface of the main body; a distal anchor including: a first wing having a first inner end and a first outer end, and a second wing having a second inner end and a second outer end, wherein the first inner end is rotatably connected to the second inner end at a first pivot point; and an internal plunger having a proximal end and a distal end, the internal plunger housed within the central bore of the main body, the distal end of the internal plunger connected to both a proximal end of a first linkage and a proximal end of a second linkage at a second pivot point, placing the spinal implant in a patient at a desired treatment site; and sliding the internal plunger distally along the longitudinal axis to rotate the first outer end of the first wing and the second outer end of the second wing distally to a second open configuration.

(B2) For the method denoted as (B1), further comprising: sliding the internal plunger proximally along the longitudinal axis to fold the first wing and the second wing proximally towards the first closed configuration to engage the first wing and the second wing with bone or tissue at the treatment site.

(B3) For the method denoted as (B1) or (B2), further comprising: moving the nut distally along the main body to engage a distal side of the nut with tissue or bone.

(B4) For the method denoted as any of (B1) through (B3), further comprising: sliding the internal plunger proximally along the longitudinal axis to move the first wing and the second wing to the first closed configuration to withdraw the spinal implant from the patient.

(C1) A spinal implant comprising: a main body having a central bore and a longitudinal axis extending between a proximal end and a distal end; a proximal anchor including a nut having a textured distal surface, the nut received around an outer surface of the main body; a distal anchor having a first closed configuration and a second open configuration, the distal anchor including: a first wing having a first inner end, a first outer end, a first substantially planar top surface, and a first base surface at the first inner end, the first top surface extending at an angle of about 35 to about 45 degrees relative to the first base surface, and a second wing having a second inner end, a second outer end, a second substantially planar top surface, and a second base surface, the second top surface extending at an angle of about 35 to about 45 degrees relative to the second base surface, wherein the first inner end is rotatably connected to the second inner end at a first pivot point; and an internal plunger having a proximal end and a distal end, the internal plunger housed within the central bore of the main body, the distal end of the internal plunger connected to both a proximal end of a first linkage and a proximal end of a second linkage at a second pivot point, wherein longitudinal distal movement of the internal plunger rotates the first outer end of the first wing and the second outer end of the second wing distally to transition from the first closed configuration to the second open configuration, and longitudinal proximal movement of the internal plunger folds the first wing and the second wing proximally to transition from the second open configuration to the first closed configuration.

(C2) For the spinal implant denoted as (C1), wherein the first wing and the second wing form an angle of about 60 degrees with respect to the main body in the second open configuration.

Although the invention has been described with reference to the embodiments illustrated in the attached drawing figures, it is noted that equivalents may be employed and substitutions made herein without departing from the scope of the invention as recited in the claims.

Having thus described various embodiments of the invention, what is claimed as new and desired to be protected by Letters Patent includes the following:

1. A spinal implant comprising:
   a main body having a central bore and a longitudinal axis extending between a proximal end and a distal end;
   a proximal anchor comprising a nut received on an outer surface of the main body;
   a distal anchor having a first closed configuration and a second open configuration, said distal anchor comprising: a first wing having a first inner end and a first outer end, and a second wing having a second inner end and a second outer end, wherein said first inner end of the first wing is pivotably connected to said second inner end of the second wing at a first pivot point; and
   an internal plunger having a proximal end and a distal end, said internal plunger housed within the central bore of the main body, said distal end of the internal plunger pivotably connected to both a proximal end of a first linkage and a proximal end of a second linkage at a second pivot point, wherein a distal end of said first linkage is pivotably connected to the distal anchor at a third pivot point located near the first inner end of the first wing, wherein a first distance between the first pivot point and the third pivot point is less than a second distance between the second pivot point and the third pivot point, and a distal end of said second linkage is pivotably connected to the distal anchor at a fourth pivot point located near the second inner of the second wing, wherein a third distance between the first pivot point and the fourth pivot point is less than a fourth distance between the second pivot point and the fourth pivot point; and wherein longitudinal distal movement of the internal plunger (i) pivots the first outer end of the first wing and the second outer end of the second wing distally about the first pivot point and (ii) pivots the first linkage and the second linkage proximally about the second pivot point, to transition from the first closed configuration to the second open configuration, and wherein longitudinal proximal movement of the internal plunger (iii) pivots the first wing and the second wing proximally about the first pivot point and (iv) pivots the first linkage and the second linkage distally about the second pivot point, to transition from the second open configuration to the first closed configuration.

2. The spinal implant of claim 1, wherein the second open configuration comprises the third pivot point and the fourth pivot point being located at a longitudinally distal position relative to the first pivot point.

3. The spinal implant of claim 2, wherein the first wing comprises a first slot on an inner surface for receiving a first medial portion of the first linkage therein, the first medial portion disposed between the second pivot point and the third pivot point, and the second wing comprises a second slot on an inner surface for receiving a second medial portion of the second linkage therein, the second medial portion disposed between the second pivot point and the fourth pivot point.

4. The spinal implant of claim 1, wherein in the first closed configuration, a maximum cross-sectional width of the distal anchor is less than a cross-sectional width of the main body.

5. The spinal implant of claim 4, wherein the first wing and the second wing form an angle of 60 degrees, or an angle of 80 degrees to 90 degrees with respect to the main body in the second open configuration.

6. The spinal implant of claim 1, wherein the distal end of the internal plunger comprises:
a first arm, a second arm, and a space between the first arm and the second arm,
wherein the proximal end of the first linkage and the proximal end of the second linkage are mounted in the space between the first arm and the second arm of the internal plunger.

7. The spinal implant of claim 1, wherein the first linkage and the second linkage respectively comprise at least one of: a concave curved bottom edge or a concave curved top edge.

8. The spinal implant of claim 1, wherein:
the first wing comprises a first planar top surface and a first base surface at the first inner end, the first planar top surface extending at an angle of 35 to 45 degrees relative to the first base surface; and/or
the second wing comprises a second planar top surface and a second base surface at the second inner end, the second planar top surface extending at an angle of 35 to 45 degrees relative to the second base surface.

9. The spinal implant of claim 8, wherein in the first closed configuration, (i) the third pivot point and the fourth pivot point are respectively located between a longitudinally distal portion of the first planar top surface and a longitudinally distal position of the second planar top surface, and (ii) the second pivot point is located between a longitudinally proximal portion of the first planar top surface and a longitudinally proximal portion of the second planar top surface.

10. The spinal implant of claim 1, wherein:
in the second open configuration, the second pivot point is located at a longitudinally proximal position relative to the first wing and the second wing, and
the first linkage and the second linkage form an angle of 45 degrees in the second open configuration, and/or the first linkage and the second linkage form an angle of 25 degrees in the first closed configuration.

11. The spinal implant of claim 1, wherein in the first closed configuration, the first outer end of the first wing and the second outer end of the second wing are located at a longitudinally proximal position relative to the second pivot point, and in the second open configuration, the first outer end of the first wing and the second outer end of the second wing are located at a longitudinally distal position relative to the second pivot point.

12. The spinal implant of claim 1, wherein:
the first linkage and the second linkage form an angle of 35 degrees in the second open configuration; and/or
the first linkage and the second linkage form an angle of 85 degrees in the second open configuration.

13. The spinal implant of claim 1, wherein at least one of the first outer end of the first wing or the second outer end of the second wing respectively comprises at least one pointed protrusion adapted to engage tissue or bone.

14. The spinal implant of claim 1, wherein a distal side of the nut comprises a textured surface adapted to engage tissue or bone.

15. A method of placing a spinal implant at a treatment site comprising:
providing a spinal implant in a first closed configuration, said spinal implant comprising:
a main body having a central bore and a longitudinal axis extending between a proximal end and a distal end;
a proximal anchor comprising a nut received on an outer surface of the main body;
a distal anchor comprising: a first wing having a first inner end and a first outer end, and a second wing having a second inner end and a second outer end, wherein said first inner end of the first wing is pivotably connected to said second inner end of the second wing at a first pivot point; and
an internal plunger having a proximal end and a distal end, said internal plunger housed within the central bore of the main body, said distal end of the internal plunger pivotably connected to both a proximal end of a first linkage and a proximal end of a second linkage at a second pivot point,
wherein a distal end of said first linkage is pivotably connected to the distal anchor at a third pivot point located near the first inner end of the first wing, wherein a first distance between the first pivot point and the third pivot point is less than a second distance between the second pivot point and the third pivot point, and a distal end of said second linkage is pivotably connected to the distal anchor at a fourth pivot point located near the second inner of the second wing, wherein a third distance between the first pivot point and the fourth pivot point is less than a fourth distance between the second pivot point and the fourth pivot point; and placing the spinal implant in a patient at a treatment site; and sliding the internal plunger distally along the longitudinal axis to (i) pivot the first outer end of the first wing and the second outer end of the second wing distally about the first pivot point and (ii) pivot the first linkage and the second linkage proximally about the second pivot point, to transition the spinal implant from the first closed configuration to a second open configuration.

16. The method of claim 15, further comprising:

sliding the internal plunger proximally along the longitudinal axis to pivot the first wing and the second wing proximally towards the first closed configuration to engage the first wing and the second wing with bone or tissue at a distal side of the treatment site.

17. The method of claim 16, further comprising:

moving the nut distally along the main body to engage a distal side of the nut with tissue or bone at a proximal side of the treatment site.

18. The method of claim 16, further comprising:

sliding the internal plunger proximally along the longitudinal axis to move the first wing and the second wing to the first closed configuration to withdraw the spinal implant from the patient.

19. A spinal implant comprising:

a main body having a central bore and a longitudinal axis extending between a proximal end and a distal end;

a proximal anchor comprising a nut having a textured distal surface, said nut received around an outer surface of the main body;

a distal anchor having a first closed configuration and a second open configuration, said distal anchor comprising:

a first wing having a first inner end, a first outer end, a first planar top surface, and a first base surface at the first inner end, the first planar top surface extending at an angle of 35 to 45 degrees relative to the first base surface, and a second wing having a second inner end, a second outer end, a second planar top surface, and a second base surface, the second planar top surface extending at an angle of 35 to 45 degrees relative to the second base surface, wherein said first inner end of the first wing is pivotably connected to said second inner end of the second wing at a first pivot point; and an internal plunger having a proximal end and a distal end, said internal plunger housed within the central bore of the main body, said distal end of the internal plunger pivotably connected to both a proximal end of a first linkage and a proximal end of a second linkage at a second pivot point, wherein a distal end of said first linkage is pivotably connected to the distal anchor at a third pivot point located near the first inner end of the first wing, wherein a first distance between the first pivot point and the third pivot point is less than a second distance between the second pivot point and the third pivot point, and a distal end of said second linkage is pivotably connected to the distal anchor at a fourth pivot point located near the second inner of the second wing, wherein a third distance between the first pivot point and the fourth pivot point is less than a fourth distance between the second pivot point and the fourth pivot point; and wherein longitudinal distal movement of the internal plunger (i) pivots the first outer end of the first wing and the second outer end of the second wing distally about the first pivot point and (ii) pivots the first linkage and the second linkage proximally about the second pivot point, to transition from the first closed configuration to the second open configuration, and wherein longitudinal proximal movement of the internal plunger (iii) pivots the first wing and the second wing proximally about the first pivot point and (iv) pivots the first linkage and the second linkage distally about the second pivot point, to transition from the second open configuration to the first closed configuration.

20. The spinal implant of claim 19, wherein in the first closed configuration, a maximum cross-sectional width of the distal anchor is less than a cross-sectional width of the main body, and wherein in the second open configuration, the second pivot point is located at a longitudinally proximal position relative to the first wing and the second wing; and wherein the first wing and the second wing form an angle of 60 degrees, or an angle of 80 degrees to 90 degrees, with respect to the main body in the second open configuration.

* * * * *